(12) United States Patent
Wood et al.

(10) Patent No.: US 11,147,616 B2
(45) Date of Patent: Oct. 19, 2021

(54) LIQUID FILLED ABLATION CATHETER WITH OVERJACKET

(71) Applicant: Ra Medical Systems, Inc., Carlsbad, CA (US)

(72) Inventors: Zachary Wood, Encinitas, CA (US); James B. Laudenslager, San Marcos, CA (US)

(73) Assignee: RA MEDICAL SYSTEMS, INC., Carlsbad, CA (US)

( * ) Notice: Subject to any disclaimer, the term of this patent is extended or adjusted under 35 U.S.C. 154(b) by 35 days.

(21) Appl. No.: 16/359,889

(22) Filed: Mar. 20, 2019

(65) Prior Publication Data

US 2019/0290356 A1 Sep. 26, 2019

Related U.S. Application Data

(60) Provisional application No. 62/646,869, filed on Mar. 22, 2018.

(51) Int. Cl.

| | |
|---|---|
| *A61B 18/14* | (2006.01) |
| *A61B 18/24* | (2006.01) |
| *A61M 25/01* | (2006.01) |
| *A61B 18/20* | (2006.01) |
| *A61B 5/283* | (2021.01) |
| *A61B 18/00* | (2006.01) |

(52) U.S. Cl.
CPC .......... *A61B 18/1492* (2013.01); *A61B 5/283* (2021.01); *A61B 18/20* (2013.01); *A61B 18/24* (2013.01); *A61B 2018/00351* (2013.01); *A61B 2018/00577* (2013.01); *A61B 2018/00791* (2013.01); *A61B 2018/206* (2013.01); *A61M 25/0108* (2013.01)

(58) Field of Classification Search
None
See application file for complete search history.

(56) References Cited

U.S. PATENT DOCUMENTS

| | | |
|---|---|---|
| 3,740,113 A | 6/1973 | Cass |
| 3,995,934 A | 12/1976 | Nath |
| 4,009,382 A | 2/1977 | Nath |
| 4,045,119 A | 8/1977 | Eastgate |

(Continued)

FOREIGN PATENT DOCUMENTS

| | | |
|---|---|---|
| CN | 1652722 A | 8/2005 |
| CN | 1832708 A | 9/2006 |

(Continued)

OTHER PUBLICATIONS

"Prevalence and Cost of ESRD Therapy," USRDS Annual Data Report 1991, American Journal of Kidney Diseases, vol. 18, No. 5, Suppl 2, (November), 1991; pp. 21-29.

(Continued)

*Primary Examiner* — Brian T Gedeon
(74) *Attorney, Agent, or Firm* — Schmeiser, Olsen & Watts LLP

(57) ABSTRACT

Outer jacket embodiments for reinforcing liquid core laser ablation catheter embodiments discussed herein may be used to improve the robustness of the laser ablation catheter embodiments. Method embodiments for making reinforced laser ablation catheters having outer jackets are also discussed.

37 Claims, 17 Drawing Sheets

(56) References Cited

U.S. PATENT DOCUMENTS

| | | | |
|---|---|---|---|
| 4,380,460 A | 4/1983 | Otstot et al. | |
| 4,516,972 A | 5/1985 | Samson et al. | |
| 4,530,569 A | 7/1985 | Squire | |
| 4,641,912 A | 2/1987 | Goldenberg | |
| 4,686,979 A | 8/1987 | Gruen et al. | |
| 4,720,166 A | 1/1988 | Ohmori et al. | |
| 4,732,448 A | 3/1988 | Goldenberg | |
| 4,739,768 A | 4/1988 | Engleson | |
| 4,747,405 A | 5/1988 | Leckrone | |
| 4,747,662 A | 5/1988 | Fitz | |
| 4,762,129 A | 8/1988 | Bonzel | |
| 4,770,653 A | 9/1988 | Shturman | |
| 4,784,132 A | 11/1988 | Fox et al. | |
| 4,784,135 A | 11/1988 | Blum et al. | |
| 4,793,359 A | 12/1988 | Sharrow | |
| 4,799,754 A | 1/1989 | Goldenberg | |
| 4,800,876 A | 1/1989 | Fox et al. | |
| 4,834,093 A | 5/1989 | Littleford et al. | |
| 4,844,062 A | 7/1989 | Wells | |
| 4,848,336 A | 7/1989 | Fox et al. | |
| 4,850,351 A | 7/1989 | Herman et al. | |
| 4,862,886 A | 9/1989 | Clarke et al. | |
| 4,907,133 A | 3/1990 | Nath | |
| 4,913,142 A | 4/1990 | Kittrell et al. | |
| 4,919,508 A | 4/1990 | Grace et al. | |
| 4,927,231 A | 5/1990 | Levatter | |
| 4,930,863 A | 6/1990 | Croitoriu et al. | |
| 4,998,794 A | 3/1991 | Holzman | |
| 5,005,944 A | 4/1991 | Laakmann et al. | |
| 5,037,404 A | 8/1991 | Gold et al. | |
| 5,040,548 A | 8/1991 | Yock | |
| 5,041,108 A | 8/1991 | Fox et al. | |
| 5,061,273 A | 10/1991 | Yock | |
| 5,076,659 A | 12/1991 | Bekiarian et al. | |
| 5,100,388 A | 3/1992 | Behl et al. | |
| 5,157,750 A | 10/1992 | Grace et al. | |
| 5,165,773 A | 11/1992 | Nath | |
| 5,176,674 A | 1/1993 | Hofmann | |
| 5,188,632 A | 2/1993 | Goldenberg | |
| 5,263,952 A | 11/1993 | Grace et al. | |
| 5,267,341 A | 11/1993 | Shearin | |
| 5,267,993 A | 12/1993 | Grace et al. | |
| 5,290,277 A | 3/1994 | Vercimak et al. | |
| 5,304,171 A | 4/1994 | Gregory et al. | |
| 5,321,783 A | 6/1994 | Nielson et al. | |
| 5,350,395 A | 9/1994 | Yock | |
| 5,395,361 A | 3/1995 | Fox et al. | |
| 5,412,750 A | 5/1995 | Nath | |
| 5,419,760 A | 5/1995 | Narcisco, Jr. | |
| 5,429,604 A | 7/1995 | Hammersmark et al. | |
| 5,429,617 A | 7/1995 | Hammersmark et al. | |
| 5,438,873 A | 8/1995 | Wlodarczyk et al. | |
| 5,456,680 A | 10/1995 | Taylor et al. | |
| 5,484,433 A | 1/1996 | Taylor et al. | |
| 5,497,441 A | 3/1996 | Croitoru et al. | |
| 5,514,128 A | 5/1996 | Hillsman et al. | |
| 5,573,531 A | 11/1996 | Gregory | |
| 5,584,558 A | 12/1996 | Nath | |
| 5,675,689 A | 10/1997 | Nath | |
| 5,722,972 A | 3/1998 | Power | |
| 5,737,473 A | 4/1998 | Nath | |
| 5,836,940 A | 11/1998 | Gregory | |
| 5,857,052 A | 1/1999 | Nath | |
| 5,868,665 A | 2/1999 | Biggs | |
| 5,989,243 A | 11/1999 | Goldenberg | |
| 6,022,309 A | 2/2000 | Celliers et al. | |
| 6,106,510 A | 8/2000 | Lunn et al. | |
| 6,117,128 A | 9/2000 | Gregory | |
| 6,143,013 A | 11/2000 | Samson et al. | |
| 6,163,641 A | 12/2000 | Eastgate | |
| 6,165,163 A | 12/2000 | Chien et al. | |
| 6,212,422 B1 | 4/2001 | Berg et al. | |
| 6,263,236 B1 | 7/2001 | Kasinkas et al. | |
| 6,306,124 B1 | 10/2001 | Jones et al. | |
| 6,314,226 B1 | 11/2001 | Nath | |
| 6,314,227 B1 | 11/2001 | Nath | |
| 6,368,318 B1 | 4/2002 | Visuri et al. | |
| 6,418,257 B1 | 7/2002 | Nath | |
| 6,507,688 B1 | 1/2003 | Nath | |
| 6,520,934 B1 | 2/2003 | Lee et al. | |
| 6,571,049 B1 | 5/2003 | Nath | |
| 6,585,760 B1 | 7/2003 | Fogarty | |
| 6,609,014 B1 | 8/2003 | Allison et al. | |
| 6,824,553 B1 * | 11/2004 | Samson | A61M 25/005 606/192 |
| 6,893,427 B1 * | 5/2005 | Jimenez | A61L 29/14 604/525 |
| 6,963,688 B2 | 11/2005 | Nath | |
| 6,974,473 B2 | 12/2005 | Barclay et al. | |
| 7,050,692 B2 | 5/2006 | Harlen et al. | |
| 7,144,248 B2 | 12/2006 | Irwin | |
| 7,144,381 B2 | 12/2006 | Gertner | |
| 7,167,622 B2 | 1/2007 | Temelkuran et al. | |
| 7,402,151 B2 | 7/2008 | Rosenman et al. | |
| 7,572,254 B2 | 8/2009 | Hebert et al. | |
| 7,762,980 B2 | 7/2010 | Gertner | |
| 8,152,795 B2 | 4/2012 | Farr et al. | |
| 8,231,551 B2 | 7/2012 | Griffin et al. | |
| 8,652,084 B2 | 2/2014 | Akingba | |
| 9,339,628 B2 | 5/2016 | Adams et al. | |
| 9,700,655 B2 * | 7/2017 | Laudenslager | A61L 29/041 |
| 9,962,527 B2 | 5/2018 | Laudenslager et al. | |
| 10,384,038 B2 | 8/2019 | Laudensalger et al. | |
| 10,478,251 B2 | 11/2019 | Shuffler et al. | |
| 10,485,613 B2 | 11/2019 | Hendrick et al. | |
| 10,492,876 B2 | 12/2019 | Anastassiou et al. | |
| 10,555,772 B2 | 2/2020 | Laudenslger et al. | |
| 10,799,671 B2 | 10/2020 | Shimada et al. | |
| 2003/0023236 A1 | 1/2003 | Gowda et al. | |
| 2003/0078569 A1 | 4/2003 | Caldera et al. | |
| 2003/0158561 A1 | 8/2003 | Kanesaka | |
| 2004/0220473 A1 | 11/2004 | Lauldi | |
| 2005/0031281 A1 | 2/2005 | Nath | |
| 2005/0254237 A1 | 11/2005 | Nath et al. | |
| 2006/0253048 A1 | 11/2006 | Jones et al. | |
| 2006/0271090 A1 | 11/2006 | Shaked et al. | |
| 2007/0244495 A1 | 10/2007 | Kwon | |
| 2008/0188793 A1 * | 8/2008 | Kozak | A61B 17/32037 604/22 |
| 2008/0249515 A1 | 10/2008 | Taylor | |
| 2009/0112198 A1 | 4/2009 | Khanna et al. | |
| 2009/0163899 A1 | 6/2009 | Burton et al. | |
| 2009/0227997 A1 | 9/2009 | Wang et al. | |
| 2009/0254074 A1 | 10/2009 | Splinter | |
| 2009/0264898 A1 | 10/2009 | Miller et al. | |
| 2010/0004607 A1 | 1/2010 | Wilson et al. | |
| 2010/0016842 A1 | 1/2010 | Fix | |
| 2010/0087783 A1 | 4/2010 | Weber et al. | |
| 2010/0114081 A1 | 5/2010 | Keeler et al. | |
| 2010/0152720 A1 | 6/2010 | Sauro et al. | |
| 2010/0198193 A1 | 8/2010 | Trapp | |
| 2011/0238041 A1 * | 9/2011 | Lim | A61M 25/0054 604/527 |
| 2012/0277671 A1 * | 11/2012 | Fuentes | A61M 25/005 604/95.04 |
| 2013/0096545 A1 | 4/2013 | Laudenslager et al. | |
| 2015/0057639 A1 | 2/2015 | Storbeck et al. | |
| 2015/0105714 A1 | 4/2015 | Laudenslager et al. | |
| 2017/0143424 A1 | 5/2017 | Laudenslager et al. | |
| 2017/0266351 A1 | 9/2017 | Laudenslager et al. | |
| 2018/0008348 A1 | 1/2018 | Grace et al. | |
| 2018/0021550 A1 | 1/2018 | Laudenslager et al. | |
| 2018/0021551 A1 | 1/2018 | Laudenslager et al. | |
| 2018/0021552 A1 | 1/2018 | Laudenslager et al. | |
| 2018/0250498 A1 | 9/2018 | Stern et al. | |
| 2019/0142517 A1 | 5/2019 | Chia et al. | |
| 2019/0160259 A1 | 5/2019 | Cottone et al. | |
| 2019/0290356 A1 | 9/2019 | Wood et al. | |
| 2019/0366036 A1 | 12/2019 | Jalgaonkar et al. | |
| 2020/0046429 A1 | 2/2020 | Tschida et al. | |

(56) References Cited

U.S. PATENT DOCUMENTS

| | | | |
|---|---|---|---|
| 2020/0230294 | A1 | 7/2020 | Laudenslager et al. |
| 2020/0261154 | A1 | 8/2020 | Ogata et al. |

FOREIGN PATENT DOCUMENTS

| | | |
|---|---|---|
| EP | 0247746 | 12/1987 |
| EP | 0368512 | 5/1990 |
| EP | 0590268 | 4/1994 |
| EP | 0727054 | 8/1996 |
| EP | 1757428 | 2/2007 |
| EP | 2301617 | 3/2011 |
| WO | WO 95/012138 | 5/1995 |
| WO | WO 97/039691 | 10/1997 |
| WO | WO 98/038538 | 9/1998 |
| WO | WO 00/030696 | 6/2000 |
| WO | WO 09/120871 | 10/2009 |

OTHER PUBLICATIONS

Bittl; Catheter Interventions for Hemodiaylysis Fistulas and Grafts: J Am Coll Cardiol Intv vol. 3 pp. 1-11 (2010).
Das, "Excimer Laser-Assisted Angioplasty for Infrainguinal Artery Disease" J of Endovasc Therapy vol. 16 pp. 1198-11104(2009).
Drooz, "Ultrahigh-pressure angioplasty of a transposed brachiocephalic fistula with recurrent stenosis," ConQuest PTA Dilation Catheter, Bard Peripheral Vascular, Inova Fairfax Hospital; Fairfax, VA, Aug. 2005.
Forauer, Hoffer, et al.; "Dialysis Access Venous Stenoses: Treatment with Balloon Angioplasty-1—versus 3-minute Inflation Times" Radiology vol. 249, pp. 375-381 (2008).
Gandini and Del Giudice; "Use of laser Atherectomy with drug-eluting balloon angioplasty shows benefit in treatment of in-stent restenosis" presented at EuroPCR 2014 Congress (May 20-23, 2014), Paris, France.
Haage, Verwerk et al.:"Percutaneous treatment of thrombosed primary arteriovenous hemodialysis access fistulae" Kidney International, vol. 57, pp. 1169-1175(2000).
Hamburger et al., New Aspects of Excimer Laser Coronary Angioplasty Physical Aspects and Clinical Results, printed by Optima Grafische Communicatie ISBN 90-73235-27-8, Rotterdam, Jaap N. Hamburger, Dec. 1998.
Hofstra et al., "Enhanced Cellular Proliferation in Intact Stenotic Lesions Derived From Human Arteriovenous Fistulas and peripheral Bypass Grafts. Does it correlate with Flow Parameters?" Circulation, 1996;94:1283-1290.
Janis et al. "Laser Thrombolysis in an in vitro Model" Lasers in Surg.: Advanced Characterization, Therapeutics and Systems, Pro. Of SPIE vol. 3907 pp. 582-585 (2000).
Ma et al., "Interaction of excimer laser with blood components and thrombosis" Life Science J. vol. 5 pp. 19-26 (2008).
Mickley; "Stenosis and thrombus in hemodialysis fistulae and grafts: the surgeon's point of view" Nephrol Dial Transplant vol. 19 pp. 309-311 (2004).
Miller and Friedman, "Balloon-Assisted Maturation of Arteriovenous Fistulas" Endovascular Today Endovascular Today, pp. 46-54 (2010).
Morph® "Universal Deflectable Guide Catheter," BioCardia® Cat # 01037-5.
Mysliwiec, "Vascular access thrombosis—what are the possibilities of intervention?" Nephrol Dial Transplant (1997) 12: Editorial Comments.
Ozkan, Gungor et al. "Endovascular Stent Placement of Juxtaanastomotic Stenosis in Native Arteriovenus Fistula After Unsuccessful Balloon Angioplasty" Iranian J of Radiology, vol. 10 pp. 133-139 (2013).
Papaioannou et al. "Excimer Laser Assisted Thrombolysis: The Effect of Fluence, Repetition Rate and Catheter Size" Proc. SPIE 4609, Lasers in Surgery; Advanced Characterization, Therapeutics and Systems XII 413 (2002).
Papaioannou et al. "Particulate debris analysis during excimer laser thrombolysis: An in-vitro study" Proc. SPIE 4609, Lasers in Surgery; Advanced Characterization, Therapeutics and Systems XII 404 (2002).
Shenoy, "Surgical anatomy of upper arm: what is needed for AVF planning" J of Vascul Access vol. 10 pp. 223-232(2009).
Sofocleous et al.;"Dialysis Fistulas" In Medscape (2013).
Staniloae et al., "Obrital Atherectomy: Device Evolution and Clinical Data" Periperal Vasc. Disease, vol. 26, pp. 215-219 (2014).
Van den Berg, Pedrotti et al.; "In-Stent Restenosis: Mid-Term Results of Debulking Using Excimer Laser and Drug-Eluting Balloons: Sustained Benefit?" J Invasive Cardiol vol. 26 pp. 333-337(2014).
Van den Berg; "Atherectomy and DCB in the SFA: A Summary of the Data" Endovascular Today pp. 28-32(2014).
Walker et al., "Excimer Laser-Assisted Angioplasty" Endovasc. Today,pp. 75-76(2007).
Zaleski; "Declotting, Maintenance, and Avoiding Procedural Complications of Native Arteriovenus Fistulae" Semin Intervent Radiol. vol. 21, pp. 83-93 (2004).
Zwaan et al., "Initial clinical experience with a new pulsed dye laser device in angioplasty of limb ischemia and shunt fistula obstructions," European Journal of Radiology, 14 (1992) pp. 72-76.
Extended European Search Report dated May 29, 2015 in European Patent Application No. EP 12840010.8, filed: Oct. 12, 2012.
International Preliminary Report on Patentability dated: Apr. 24, 2014 in International Application No. PCT/US2012/060065 filed Oct. 12, 2012.
International Search Report and Written Opinion dated: Mar. 29, 2013 in International Application No. PCT/US2012/060065 filed Oct. 12, 2012.
Notice of Allowance dated: Jan. 30, 2018 in U.S. Appl. No. 14/515,435, filed Oct. 15, 2014, published as: 2015/0105714 dated Apr. 16, 2015 and now U.S. Pat. No. 9,962,527 dated May 8, 2018.
ExParte Quayle Action dated: Dec. 12, 2017 in U.S. Appl. No. 14/515,435, filed Oct. 15, 2014, published as: 2015/0105714 on Apr. 16, 2015 and issued as: U.S. Pat. No. 9,962,527 on May 8, 2018.
Notice of Allowance dated: Apr. 19, 2019 in U.S. Appl. No. 15/723,062, filed Oct. 2, 2017, published as: 2018/0021551 dated Jan. 25, 2018.
Non Final Office Action dated: Dec. 31, 2018 in U.S. Appl. No. 15/723,062, filed Oct. 2, 2017, published as: 2018/0021551 dated Jan. 25, 2018.
Non Final Office Action dated: Nov. 30, 2018 in U.S. Appl. No. 15/723,057, filed Oct. 2, 2017, published as: 2018/0021550 dated Jan. 25, 2018 and now U.S. Pat. No. 10,245,417 dated Apr. 2, 2019.
Notice of Allowance dated: Dec. 31, 2018 in U.S. Appl. No. 15/723,057, filed Oct. 2, 2017, published as: 2018/0021550 dated Jan. 25, 2018 and now U.S. Pat. No. 10,245,417 dated Apr. 2, 2019.
Notice of Allowance dated: Feb. 26, 2019 in U.S. Appl. No. 15/723,057, filed Oct. 2, 2017, published as: 2018/0021550 dated Jan. 25, 2018 and now U.S. Pat. No. 10,245,417 dated Apr. 2, 2019.
Notice of Allowance dated: Apr. 17, 2019 in U.S. Appl. No. 15/723,067, filed Oct. 2, 2017, published as: 2018/0021552 dated Jan. 25, 2018.
Notice of Allowance dated: Feb. 27, 2019 in U.S. Appl. No. 15/723,067, filed Oct. 2, 2017, published as: 2018/0021552 dated Jan. 25, 2018.
ExParte Quayle Action dated: Nov. 29, 2018 in U.S. Appl. No. 15/723,067, filed Oct. 2, 2017, published as: 2018/0021552 on Jan. 25, 2018.
Notice of Allowance dated: Apr. 20, 2017 in U.S. Appl. No. 13/651,070, filed Oct. 12, 2012 and published as: US-2013/0096545 dated Apr. 18, 2013 and now U.S. Pat. No. 9,700,655 dated Jul. 11, 2017.
Final Office Action dated: Sep. 15, 2016 in U.S. Appl. No. 13/651,070, filed Oct. 12, 2012 and published as: US-2013/0096545 dated Apr. 18, 2013 and now U.S. Pat. No. 9,700,655 dated Jul. 11, 2017.
Non-Final Office Action dated: Feb. 12, 2016 in U.S. Appl. No. 13/651,070, filed Oct. 12, 2012 and published as: US-2013/0096545 dated Apr. 18, 2013 and now U.S. Pat. No. 9,700,655 dated Jul. 11, 2017.

(56) References Cited

OTHER PUBLICATIONS

Extended European Search Report dated Aug. 13, 2019 in European Patent Application No. EP 19163464.1, filed: Mar. 18, 2019.
Notice of Allowance dated: Oct. 17, 2019 in U.S. Appl. No. 15/359,412, filed Nov. 22, 2016, published as: 2017/0143424 dated May 25, 2017.
Non-Final Office Action dated: Aug. 5, 2019 in U.S. Appl. No. 15/359,412, filed Nov. 22, 2016, published as: 2017/0143424 dated May 25, 2017.
Non-Final Office Action dated: Sep. 9, 2020 in U.S. Appl. No. 15/615,734, filed Jun. 6, 2017 and published as: US-2017/0266351 dated Sep. 21, 2017.
Non-Final Office Action dated: Sep. 30, 2020 in U.S. Appl. No. 16/502,766, filed Jul. 3, 2019 and published as: US-2019/0336732 dated Nov. 7, 2019.
Non-Final Office Action dated: Apr. 1, 2021 U.S. Appl. No. 16/549,516, filed Aug. 23, 2019 and published as: US-2019/0374684 dated Dec. 12, 2019.
Invitation to Pay Additional Fees, dated Apr. 29, 2021 in International Patent Application No. PCT/US2021/019199 filed: Feb. 23, 2021.
International Search Report and Written Opinion dated Jul. 12, 2021 in International Patent Application: PCT/US21/19199 filed Feb. 23, 2021.

* cited by examiner

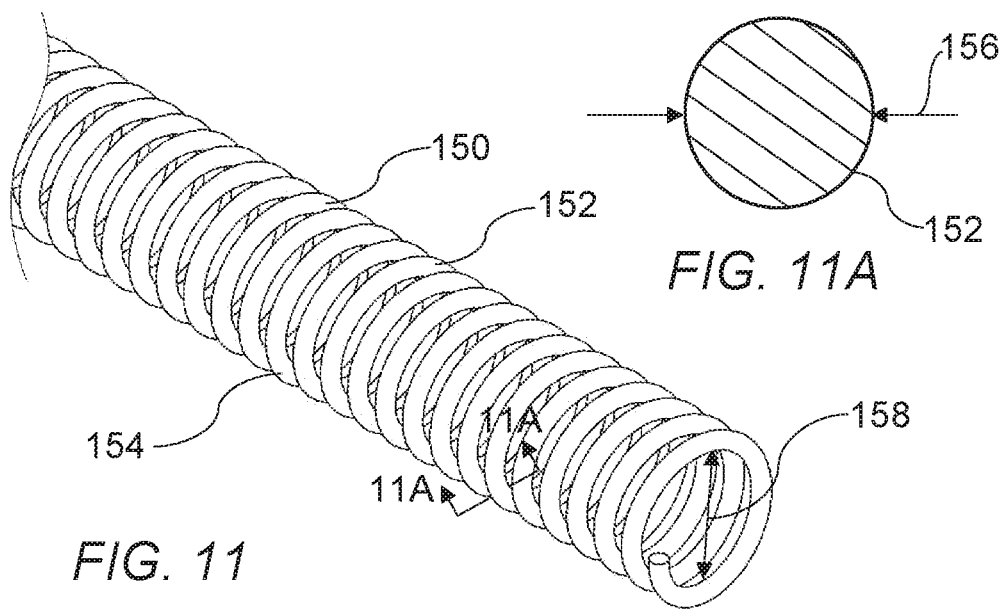
FIG. 11
FIG. 11A
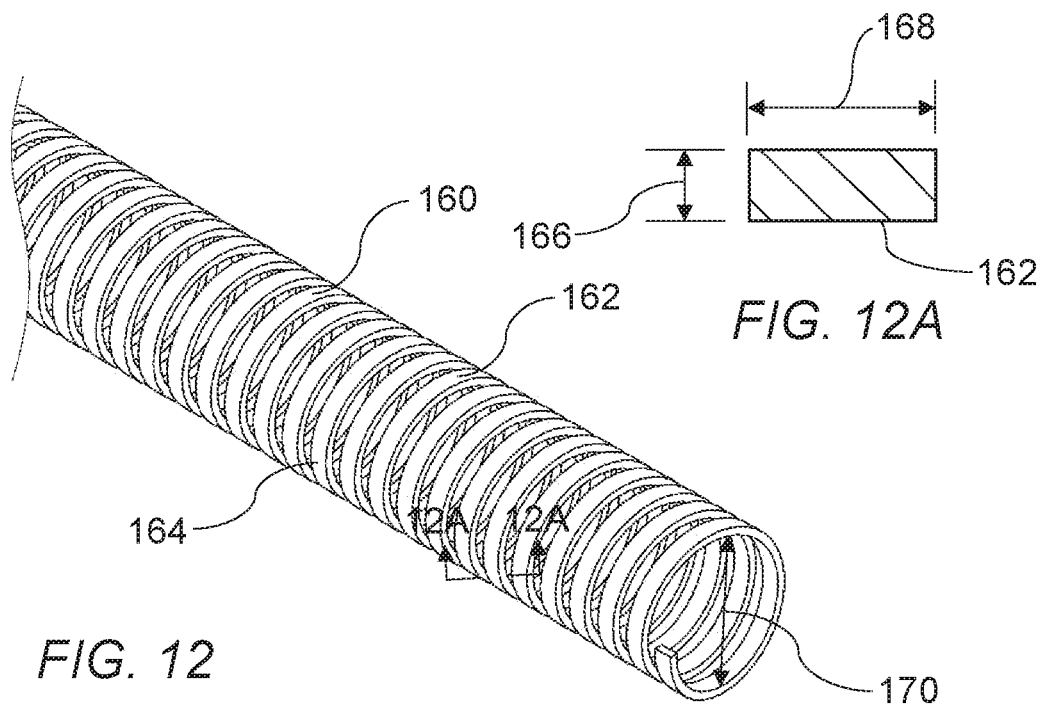
FIG. 12
FIG. 12A

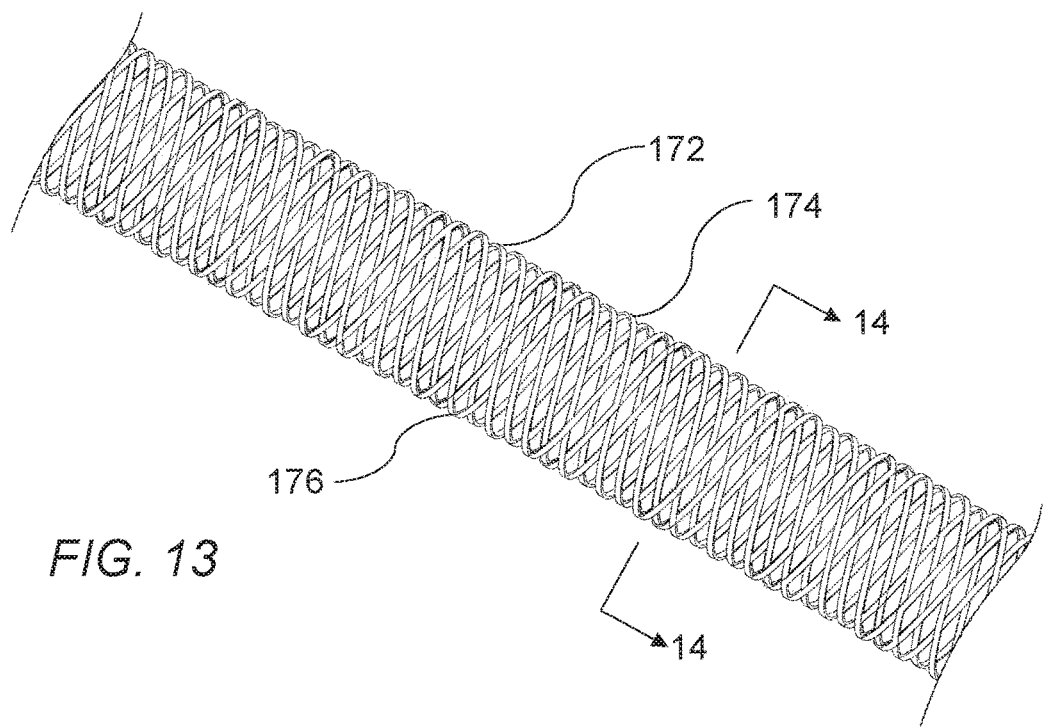
FIG. 13
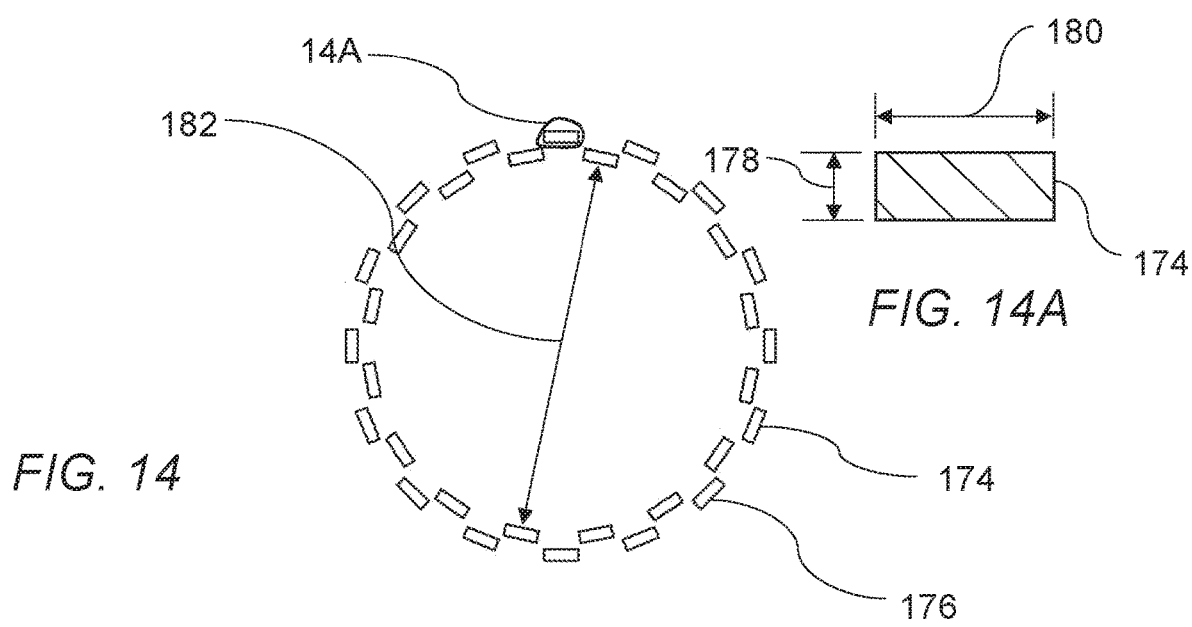
FIG. 14
FIG. 14A

LIQUID FILLED ABLATION CATHETER WITH OVERJACKET

RELATED PATENT APPLICATION

This application claims priority under 35 U.S.C. section 119(e) from U.S. provisional application Ser. No. 62/646,869, filed Mar. 22, 2018, naming Zachary Wood and James B. Laudenslager as inventors, entitled "LIQUID FILLED ABLATION CATHETER WITH OVERJACKET", which is incorporated by reference herein in its entirety.

BACKGROUND

During catheter procedures, which may include angioplasty, catheters often pass through tortuous paths of body lumens. During passage various forces may need to be applied to the medical catheter to deliver it to a target and perform a desired procedure. In some cases, a medical catheter may be inserted into a patient's body through a hemostatic support catheter, and this can result in relative friction between the support catheter and the medical catheter and therefore increase the force required to advance the medical catheter to a target site. In addition, medical catheters sometimes include fragile components such as fiber optics, electrical components or the like. As such, when a user of the medical catheter is performing a procedure, the user can sometimes deform a shaft of the medical catheter while applying the forces required to advance the medical catheter to the target site. This in turn may lead to reduced performance of the medical catheter. What have been needed are devices and methods which allow a user of a medical catheter to position the medical catheter at a target site without deforming the medical catheter shaft or components disposed within the shaft of the medical catheter. What have been needed are devices and methods that allow a medical catheter to withstand the forces required to position the medical catheter while minimizing undesired bulk to the medical catheter profile.

SUMMARY

Some embodiments of a laser ablation catheter to ablate blockages in body lumens using high energy and high-power Ultraviolet (UV) laser pulses may include a liquid filled waveguide including a catheter tube having an inner layer with a first index of refraction and a biocompatible ultraviolet transparent optical fluid disposed within and completely filling an inner lumen of the catheter tube. The optical fluid may have a second index of refraction which is greater than the first index of refraction. The laser ablation catheter may also include an ultraviolet grade elongated distal optical window which is disposed in liquid sealed relation to a surface of the catheter tube at a distal end of the catheter tube, and which is in optical communication with the optical fluid. The laser ablation catheter may also include an optical window which is disposed in a liquid sealed relation to a surface of the catheter tube at a proximal end of the catheter tube and in optical communication with the optical fluid. The laser ablation catheter may also include an outer jacket that is disposed over the surface of the catheter tube and that has a proximal end that is disposed at a proximal portion of the catheter tube and a distal end that is disposed at an axial position that is about 10 cm to about 60 cm proximal of a distal end of the catheter tube. The outer jacket may be secured relative to the catheter tube such that the outer jacket remains substantially fixed along a longitudinal axis thereof relative to the catheter tube. The outer jacket may also have a tubular configuration having an inner lumen with an inner surface, with the inner surface of the inner lumen being configured to slide over an exterior surface of the catheter tube with a close fit therebetween. The outer jacket may also include a tubular jacket body that has a longitudinal stiffness greater than a longitudinal stiffness of the catheter tube at the proximal portion of the catheter tube. The outer jacket may also include a tubular reinforcement that is crush resistant and which is disposed along the tubular jacket body, with the tubular jacket body and reinforcement being configured to increase the stiffness and crush resistance of the laser ablation catheter.

Some embodiments of a laser ablation catheter to ablate blockages in body lumens using high energy and high-power UV laser pulses may include a liquid filled waveguide including a catheter tube having an inner layer with a first index of refraction and a biocompatible ultraviolet transparent optical fluid disposed within and completely filling an inner lumen of the catheter tube. The optical fluid may have a second index of refraction which is greater than the first index of refraction. The laser ablation catheter may also include an ultraviolet grade elongated distal optical window which is disposed in liquid sealed relation to a surface of the catheter tube at a distal end of the catheter tube, and which is in optical communication with the optical fluid. The laser ablation catheter may also include an optical window which is disposed in a liquid sealed relation to a surface of the catheter tube at a proximal end of the catheter tube and in optical communication with the optical fluid. The laser ablation catheter may also include an outer jacket that is disposed over the surface of the catheter tube and that has a proximal end that is disposed at a proximal portion of the catheter tube and a distal end that is disposed at an axial position that is about 10 cm to about 60 cm proximal of a distal end of the catheter tube. The outer jacket may be secured relative to the catheter tube such that the outer jacket remains substantially fixed along a longitudinal axis thereof relative to the catheter tube. The outer jacket may have a substantially constant transverse outer dimension and may have a tubular configuration having an inner lumen with an inner surface, with the inner surface of the inner lumen being configured to slide over an exterior surface of the catheter tube with a close fit therebetween. The outer jacket may also include a tubular jacket body that has a longitudinal stiffness which is greater than a longitudinal stiffness of the catheter tube at the proximal portion of the catheter tube. The tubular jacket body may be configured in dimension, material(s) etc. to increase the stiffness and crush resistance of the laser ablation catheter along a length of the outer jacket.

Some embodiments of a laser ablation catheter to ablate blockages in body lumens using high energy and high-power UV laser pulses may include a liquid filled waveguide including a catheter tube having an inner layer with a first index of refraction and a biocompatible ultraviolet transparent optical fluid disposed within and completely filling an inner lumen of the catheter tube. The optical fluid may have a second index of refraction which is greater than the first index of refraction. The laser ablation catheter may also include an ultraviolet grade elongated distal optical window which is disposed in liquid sealed relation to a surface of the catheter tube at a distal end of the catheter tube, and which is in optical communication with the optical fluid. The laser ablation catheter may also include an optical window which is disposed in a liquid sealed relation to a surface of the catheter tube at a proximal end of the catheter tube and in optical communication with the optical fluid. The laser ablation catheter may also include an outer jacket that is disposed over the surface of the catheter tube and that has a proximal end that is disposed at a proximal portion of the catheter tube and a distal end that is disposed at an axial position that is about 10 cm to about 60 cm proximal of a distal end of the catheter tube. The outer jacket may be secured relative to the catheter tube such that the outer jacket remains substantially fixed along a longitudinal axis thereof relative to the catheter tube. The outer jacket may have a tubular configuration having an inner lumen with an inner surface, with the inner surface of the inner lumen being configured to slide over an exterior surface of the catheter tube with a close fit therebetween. The outer jacket may include a tubular jacket body that has a longitudinal stiffness greater than a longitudinal stiffness of the catheter tube at the proximal portion of the catheter tube. The tubular jacket body may include a tapered axial section that tapers distally to a smaller outer transverse dimension and cross section area, with the tubular jacket body being configured to increase the stiffness and crush resistance of the laser ablation catheter over a proximal portion of the outer jacket.

Some embodiments of a laser ablation catheter to ablate blockages in body lumens using high energy and high-power UV laser pulses may include a liquid filled waveguide including a catheter tube having an inner layer with a first index of refraction and a biocompatible ultraviolet transparent optical fluid disposed within and completely filling an inner lumen of the catheter tube. The optical fluid may have a second index of refraction which is greater than the first index of refraction. The laser ablation catheter may also include an ultraviolet grade elongated distal optical window which is disposed in liquid sealed relation to a surface of the catheter tube at a distal end of the catheter tube, and which is in optical communication with the optical fluid. The laser ablation catheter may also include an optical window which is disposed in a liquid sealed relation to a surface of the catheter tube at a proximal end of the catheter tube and in optical communication with the optical fluid. The laser ablation catheter may also include an outer jacket that is disposed over the surface of the catheter tube and that has a proximal end that is disposed at a proximal portion of the catheter tube and a distal end that is disposed at an axial position that is about 10 cm to about 60 cm proximal of a distal end of the catheter tube. The outer jacket may be secured relative to the catheter tube such that the outer jacket remains substantially fixed along a longitudinal axis thereof relative to the catheter tube. The outer jacket may have a tubular configuration having an inner lumen with an inner surface, with the inner surface of the inner lumen being configured to slide over an exterior surface of the catheter tube with a close fit therebetween. The outer jacket may also include a tubular jacket body that has a longitudinal stiffness greater than a longitudinal stiffness of the catheter tube at the proximal portion of the catheter tube. The tubular jacket body may also include a tapered axial section that tapers distally to a smaller outer transverse dimension and cross section area. The outer jacket may also include a tubular reinforcement that is crush resistant and that is disposed along the tubular jacket body, with the tubular jacket body and reinforcement being configured to increase the stiffness and crush resistance of the laser ablation catheter. The outer jacket may also include a plurality of sequential axial sections which are sequentially disposed along the longitudinal axis of the outer jacket, with each axial section including a material having a flexural modulus which is different from the flexural moduli of respective adjacent axial section materials.

Some embodiments of a laser ablation catheter to ablate blockages in body lumens using high energy and high-power UV laser pulses may include a liquid filled waveguide including a catheter tube having an inner layer with a first index of refraction and a biocompatible ultraviolet transparent optical fluid disposed within and completely filling an inner lumen of the catheter tube. The optical fluid may have a second index of refraction which is greater than the first index of refraction. The laser ablation catheter may also include an ultraviolet grade elongated distal optical window which is disposed in liquid sealed relation to a surface of the catheter tube at a distal end of the catheter tube, and which is in optical communication with the optical fluid. The laser ablation catheter may also include an optical window which is disposed in a liquid sealed relation to a surface of the catheter tube at a proximal end of the catheter tube and in optical communication with the optical fluid. The laser ablation catheter may also include an outer jacket that is disposed over the catheter tube and that has a proximal end that is disposed at a proximal portion of the catheter tube and a distal end that is disposed at an axial position which is substantially adjacent to a distal end of the catheter tube. The outer jacket being secured relative to the catheter tube such that the outer jacket remains substantially fixed along a longitudinal axis thereof relative to the catheter tube. The outer jacket may have a substantially constant transverse outer dimension and may have an inner lumen with an inner surface. The inner surface of the inner lumen may be configured to slide over an exterior surface of the catheter tube with a close fit therebetween. The outer jacket may also include a tubular jacket body that has a longitudinal stiffness greater than a longitudinal stiffness of the catheter tube at a proximal portion thereof, with the tubular jacket body formed from a jacket body material that is water impermeable and the tubular jacket body being configured to increase the stiffness and crush resistance of the laser ablation catheter along a length of the outer jacket.

Some methods for making a liquid core ablation catheter may include coating an inside surface of a catheter tube with an optical coating having a first index of refraction. Such methods may also include applying an appropriate thermal cycle to the catheter tube and the optical coating in order to adhere the optical coating to the inside surface of the catheter tube. Such methods may also include attaching an elongated distal optical window to a distal portion of the catheter tube. Such methods may also include filling the catheter tube with a biocompatible ultraviolet transparent optical fluid having a second index of refraction. Such methods may also include attaching a high energy laser coupler to a proximal portion of the catheter tube with the laser coupler having a laser coupler body, a window connector body being disposed within the optical coupler body, and an optical input window disposed within and secured to the window connector body with the optical window being in optical communication with the optical fluid. Such methods may also include transmitting laser light through the optical fluid in order to determine the optical performance of the optical coating. Such methods may also include sliding an outer jacket over the catheter tube, with the outer jacket having an inner lumen with an inner surface and the inner surface of the inner lumen being configured to slide over an exterior surface of the catheter tube with a close fit therebetween. Such methods may also include securing the outer jacket to the catheter tube such that a longitudinal axis of the outer jacket remains substantially fixed in relation the catheter tube, with the outer jacket being configured to increase the stiffness and crush resistance of the laser ablation catheter.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

FIG. 11 is a perspective view of a tubular reinforcement embodiment configured as a coiled reinforcement wire shown without additional structure of the corresponding laser ablation catheter for the purposes of illustration.

FIG. 11A is a transverse cross section view of the reinforcement wire of FIG. 11 taken across lines 11A-11A of FIG. 11.

FIG. 12 is a perspective view of a tubular reinforcement embodiment configured as a coiled reinforcement ribbon shown without additional structure of the laser ablation catheter for the purposes of illustration.

FIG. 12A is a transverse cross section view of the reinforcement ribbon of FIG. 12 taken across lines 12A-12A of FIG. 12.

FIG. 13 is a perspective view of a tubular reinforcement embodiment configured as braided reinforcement ribbons and shown without additional structure of the corresponding laser ablation catheter for the purposes of illustration.

FIG. 14 is a transverse cross section view of the tubular reinforcement embodiment of FIG. 13 taken along lines 14-14 of FIG. 13.

FIG. 14A is an enlarged view of the encircled section of the tubular reinforcement of FIG. 14.

Figure 1:
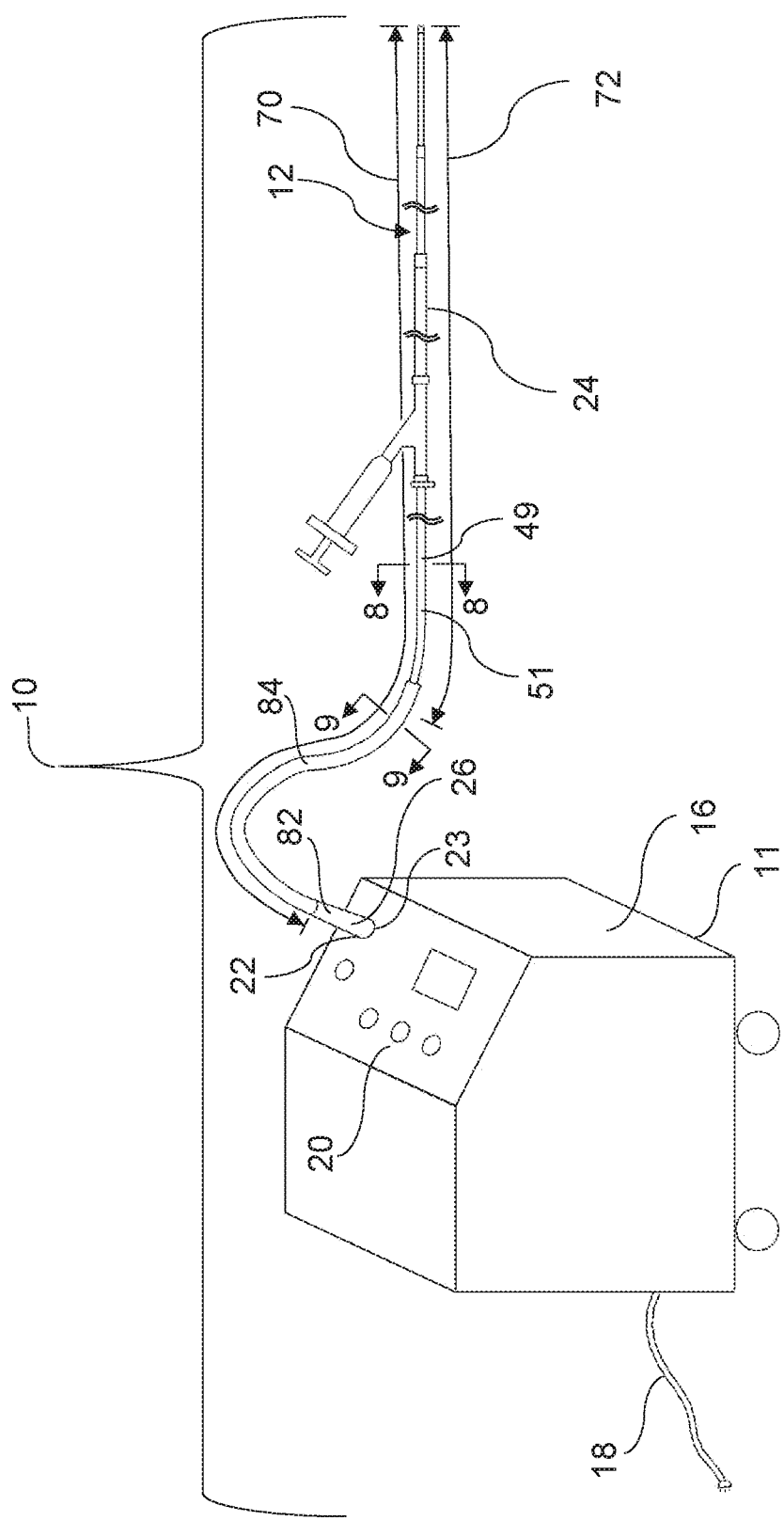
FIG. 1 is a perspective view of a laser system embodiment including a laser and a disposable laser ablation catheter coupled to the laser.

The drawings are intended to illustrate certain exemplary embodiments and are not limiting. For clarity and ease of illustration, the drawings may not be made to scale and, in some instances, various aspects may be shown exaggerated or enlarged to facilitate an understanding of particular embodiments.

DETAILED DESCRIPTION

Some embodiments of laser systems may include a laser and a disposable liquid core laser ablation catheter which may be operatively coupled to the laser. Liquid core laser ablation catheters sometimes use a low index of refraction coating which may be applied to an inner surface of a fluoropolymer catheter tube of the laser ablation catheter to yield high transmission laser energy through an optical fluid disposed within the catheter tubing. In some cases, the laser energy may have a wavelength in the ultraviolet range and in some particular cases of about 308 nm and may be pulsed in order to allow for tissue ablation by the laser ablation catheter. Some such laser system embodiments and associated laser ablation catheter embodiments are discussed in commonly owned U.S. Pat. No. 9,700,655, filed Oct. 12, 2012, by J. Laudenslager et al. and issued Jul. 11, 2017, titled "Small Flexible Liquid Core Catheter for Laser Ablation in Body Lumens and Methods for Use", U.S. Patent Publication No. 2015/0105714, Ser. No. 14/515,435, filed Oct. 15, 2014, by J. Laudenslager et al., titled "Methods and Devices for Treatment of Stenosis of Arteriovenous Fistula Shunts", and U.S. Patent Publication No. 2017/0143424, Ser. No. 15/359,412, filed Nov. 22, 2016, by J. Laudenslager et al., titled "Laser Ablation Catheters Having Expanded Distal Tip Windows for Efficient Tissue Ablation," all of which are hereby incorporated by reference herein in their entirety.

Fluoropolymers such as fluorinated ethylene propylene (FEP), ethylene-tetrafluoroethylene-hexafluoropropylene (EFEP), ethylene tetrafluoroethylene (ETFE) and others may be useful for the catheter tubing material in these types of applications because catheter tubing formed from these materials has a high UV transmission, the low index amorphous Teflon AF coatings may adhere well to the fluoropolymers, and the fluoropolymer catheter tubes may be configured to be very flexible when axial loads are applied to the laser ablation catheter. Additionally, catheter tubes which are formed from these materials may be coated with low index of refraction optical coatings in order to create an inner layer on the inner surface of the catheter tube. For some embodiments the inner layer may have a first index of refraction and an optical fluid disposed within an inner lumen of such catheter tubes may have a second index of refraction which is greater than the first index of refraction thereby forming a waveguide and allowing for high energy laser transmission through the optical fluid.

In some cases, an optical coating in liquid form may be applied to the inner surface of the catheter tube, and then the optical coating may be thermally "cured" onto the inner surface via an appropriate thermal cycle thereby creating the inner layer. This thermal cycle may be performed at elevated temperatures. In some instances such elevated temperatures may possibly degrade and/or distort laser catheter components fabricated from non-fluoropolymer polymer materials and metals whereby physical distortion or softening of the materials may occur. For this reason, it may be useful to perform the thermal cycle on the catheter tube and the optical coating prior to the addition of any other components of the corresponding laser ablation catheter which may include non-fluoropolymer polymer materials or metals of the laser ablation catheter which may be degraded by the thermal cycle.

Additionally, in some cases, the surface properties of the inner surface of a catheter tube which is formed from a fluoropolymer material may need to be altered in order to improve the adhesion of the optical coating to the inner surface. For example, the inner surface of the catheter tube may be chemically etched, plasma etched, or the like in order to obtain a desired level of adhesion between the catheter tube inner surface and the inner layer optical coating after the curing process.

As discussed above, a catheter tube which is formed from fluoropolymer material may exhibit suitable flexible behavior when subjected to axial loads, the flexibility of the catheter tube allowing for advancement of the respective laser ablation catheter through potential tortuous paths of body lumens of a patient or the like during a catheter procedure. In some cases, however, the flexibility of the catheter tube material may lead to distortion of the catheter tube which may in turn decrease the optical performance of the laser ablation catheter.

Distortion of the catheter tube may occur when a user of the laser ablation catheter applies an inward radial load to the catheter tube during manipulation of the catheter (e.g. fingers distorting/crushing an outside surface of the catheter tube while gripping the laser ablation catheter). In some other cases, distortion of the catheter tube may occur during advancement of the laser ablation catheter through a tortuous path, at which time an axial load is applied to the catheter tube. The axial load may lead to the distortion/kinking of the catheter tube due to insufficient longitudinal stiffness of the catheter tube during advancement through the tortuous path.

It may therefore be useful in some instances to implement devices and methods which increase the longitudinal stiffness and/or crush resistance of the catheter tube in order to avoid distortion of the catheter tube during a laser ablation catheter procedure. Currently some balloon catheters, fiber optic ablation catheters, and atherectomy catheters utilize guidewires which are operatively coupled to the respective catheter in order to increase the longitudinal stiffness and tractability of the catheter. Additionally, support catheters may be used to support these catheters.

For some liquid filled laser ablation catheter embodiments, a guidewire disposed through a central lumen of the catheter tube would significantly decrease the optical performance of the laser ablation catheter. The placement of an additional guidewire lumen in the center of the catheter tube may eliminate or greatly reduce the ability of the catheter to transmit laser light by total internal reflection. For this reason, it may be useful for the longitudinal stiffness of the catheter tube to be optimized or improved through other means.

For some laser ablation catheter embodiments, the longitudinal stiffness of the catheter may be increased with the addition of an outer jacket which may be operatively coupled to the catheter tube waveguide portion of the laser ablation catheter. The outer jacket may be configured such that it slides over the outer surface of the catheter tube and includes a longitudinal stiffness which is greater than a longitudinal stiffness of the catheter tube. Such outer jacket embodiments may be resistant to radial loads (crush resistant) which are applied by a user of the laser ablation catheter. Because the outer jacket is configured to slide over the catheter tube, the catheter tube and optical coating may separately be exposed to an appropriate thermal cycle to form the inner layer and resulting optical waveguide properties prior to the attachment of the outer jacket. Thus, the outer jacket may include materials which would otherwise be degraded and/or distorted during application of the thermal cycle to the catheter tube and optical coating.

As an example of the potential effects of the thermal cycle on the materials and/or components of a laser ablation catheter, some laser ablation catheter embodiments may include a fluoropolymer (FEP) catheter tube having an outer surface which may be covered with tubular reinforcement such as braided metal wire or braided metal ribbon wherein portions of the tubular reinforcement physically contact the outside surface of the catheter tube. Such a tubular reinforcement may in turn be covered by a tubular polymer outer layer which may be formed from a non-fluoropolymer material such as a polyether block amide (Pebax®).

An optical coating such as an amorphous Teflon AF® coating with a low index of refraction and which is transparent to the ultraviolet wavelengths may be applied to the inner surface of the catheter tube. In this case, the optical coating may be subjected to an appropriate thermal cycle in order to adhere it to the inner surface of the catheter tube. The adhesion occurs when a solvent such as Fluorinert FC-40® in which the Teflon AF® may be dissolved is evaporated thereby leaving the Teflon AF® deposited on the inner surface of the catheter tube. Typically, the Fluorinert FC-40® may be heated above 165 degrees centigrade (which is above the boiling point of the Fluorinert FC-40®) in order to fully vaporize the solvent. A thermal cycle consisting of immersion in air heated at 170 degrees centigrade for a duration of 1-2 hours may thereby assure full vaporization of the solvent. Additionally, heating above 165 degrees centigrade assures that the Teflon AF® coating is heated above its glass transition temperature of 160 degrees centigrade thereby prompting proper adhesion of the optical coating to the inner surface of the catheter tube.

Subjecting the material of the tubular outer layer and the material of the tubular reinforcement to such a thermal cycle may lead to the distortion and/or thermal degradation of the tubular outer layer and the tubular reinforcement. Tubular outer layer materials such as Nylon® or Pebax® have melting temperatures which are below 165 degrees centigrade and would thus be subject to thermal degradation. In order to avoid thermal degradation of the tubular outer layer, the thermal cycle can be adjusted to a temperature of 100 degrees centigrade for a duration of 4 hours in some cases. However, such a thermal cycle may be less efficient due to the cycle time that is required to vaporize the solvent and may still lead to decreased laser ablation catheter performance as described by the following.

Dissimilar materials which form the catheter tube, the tubular reinforcement, and the tubular outer layer may potentially have differing thermal expansion coefficients and may expand at different rates when subjected to thermal cycles such as those discussed above thereby limiting the quality of the coating adherence to the inner surface of the catheter tube. For example, tubular reinforcement embodiments configured as metal braided ribbon may expand during such thermal cycles while its outer diameter is simultaneously being constrained by the tubular outer layer. The expansion of the tubular reinforcement may thus lead to multiple indentations on the outer surface of the catheter tube, which in turn may lead to an uneven/distorted inner surface of the catheter tube and therefore an uneven optical coating surface which may degrade the transmission of optical laser energy through the waveguide formed therefrom.

As discussed above, some laser ablation catheter embodiments discussed herein may be configured to allow for the optical coating and catheter tube to be thermally cycled and subsequently tested prior to the addition of an outer jacket. Thus, the material and/or materials of the outer jacket may not be subjected to the thermal cycle, and can therefore be appropriately chosen and configured such that the outer jacket increases the longitudinal stiffness and crush resistance of the laser ablation catheter without degrading the properties of the finished laser ablation catheter.

An embodiment of laser system 10 including a laser ablation catheter 12 that is liquid filled and that includes an outer jacket 14 is shown in FIG. 1. The laser system 10 may include a laser source 11, a housing 16, a power cord 18, a control panel 20 and an output coupler 22. For some embodiments, the laser system 10 may be configured to deliver high energy and high-power UV laser pulses and may have a wavelength of about 308 nm. For some embodiments, the laser energy output of the laser system 10 may be pulsed in order to allow for tissue ablation by the laser ablation catheter 12. In some cases, the duration of each laser energy pulse from the laser system may be from about 10 nanoseconds to about 150 nanoseconds.

The laser ablation catheter 12 may include a laser coupler 24 which is disposed at a proximal end 23 of the laser ablation catheter 12 and which is coupled to the output coupler 22 of the laser system 10. In some cases, the laser system 10 may include a support catheter 24 which is configured to slide over the laser ablation catheter 12, the support catheter 24 providing support and guidance to the laser ablation catheter 12 during a laser ablation procedure. The laser ablation catheter 12 may also include a liquid filled waveguide which is configured for the propagation of high powered laser energy through the laser ablation catheter 12 for the purposes of ablating blockages in the human body as well as other indications. The waveguide may include a tubular catheter tube 28 having an inner lumen 30 and an inner layer 32 which is disposed on an inner surface 33 of the inner lumen 30, the material of the inner layer 32 being an optical coating having a first index of refraction.

The liquid filled waveguide may also include a biocompatible ultraviolet transparent optical fluid 34 which is disposed within and which completely fills the inner lumen 30 of the catheter tube 28. The optical fluid 34 may have a second index of refraction which is greater than the first index of refraction of the inner layer 32. The different indices of refraction of the materials at an optical boundary 36 disposed between the inner layer 32 and the optical fluid 34 allow for total internal reflection at the optical boundary 36 thereby forming an optical waveguide and permitting propagation of high powered laser energy through the waveguide. The quality of optical transmission through the waveguide may be dependent upon the surface quality of the optical boundary 36. In particular, a smooth continuous optical boundary 36 which conforms to the inner surface 33 of the inner lumen 30 of the catheter tube 28 will optically outperform a rougher more discontinuous optical boundary 36 due to scattering losses etc. For this reason, it may be desirable to maximize the smoothness and continuity of an inner surface 38 of the inner layer 32 which along with the optical fluid 34 forms the optical boundary 36.

The laser ablation catheter 12 may also include an ultraviolet grade elongated distal optical window 40 which may be disposed in liquid sealed relation to an inner surface 33 of the catheter tube 12 at a distal end 44 of the catheter tube 28. The distal optical window 40 may be in optical communication with the optical fluid 34 which is disposed within the inner lumen 30 of the catheter tube 28 thereby allowing for the transmission of laser energy from the optical fluid 34 through the distal optical window 40. For some embodiments (not shown) the distal optical window 40 may be disposed within a tubular distal housing. The distal housing may be secured to both the distal optical window 40 and to the catheter tube 28 by any suitable means, and may be formed from any suitable material. In some cases, distal housing embodiments may be formed from a metal such as stainless steel, titanium or the like, which allow for attachment of the distal optical window by crimping the distal housing to the distal optical window 40 and to the catheter tube 28. The distal housing when made from such materials may also serve as a radiopaque marker in some cases.

The laser ablation catheter 12 may also include an optical window 46 which may have a cylindrical configuration and which may be disposed within the laser coupler 24, with the optical window 46 being disposed in a liquid sealed relation to the inner surface 33 of the catheter tube 28. The optical window 46 may be in optical communication and direct contact with the optical fluid 34 thereby allowing for the optical transmission of laser energy from the laser system 10, through the optical window 46, and into the optical fluid 34. The laser energy may then be propagated through the waveguide (formed by the catheter tube 28, the inner layer 32, and the optical fluid 34), through the distal optical window 40, and thereafter be emitted from an output surface of the distal optical window 40 and into a blockage disposed within a human body or any other suitable indication.

As discussed above the materials which form the respective components of the waveguide (including the catheter tube 28, the inner layer 32, and the optical fluid 34) may be chosen such that each material is not degraded by a thermal cycle which the waveguide may be subjected to during the formation of the inner layer 32. For example, the catheter tube 28 may be formed from FEP, a material which will easily endure a 170 degree centigrade (for about a 120 minute duration in some cases) thermal cycle required to the "cure" an inner layer 32 which may in turn be formed from an amorphous Teflon AF®/Fluorinert FC-40® solution. However, catheter tubes 12 formed from thermally suitable materials such as FEP may lack the longitudinal stiffness and crush resistance which are required in order to avoid distortion/optical damage to the waveguide during a laser ablation catheter 12 procedure. The addition of an outer jacket 14 to the catheter tube 28 of the laser ablation catheter 12 allows for the separate processing of some waveguide components (including the catheter tube 28 and inner layer 32), and adds longitudinal stiffness and crush resistance to the structure of the laser ablation catheter.

Figure 2:
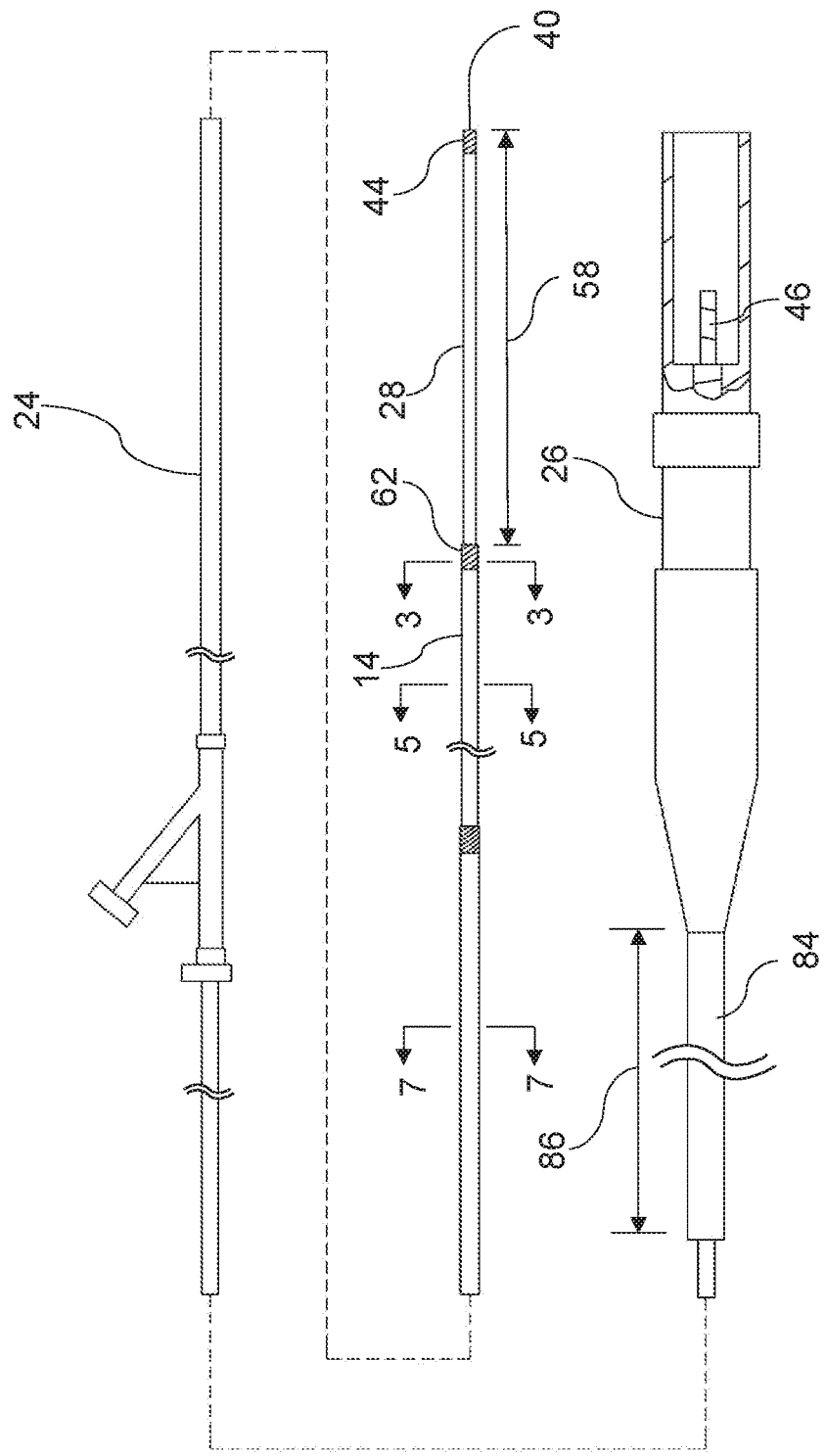
FIG. 2 is an elevation view in partial section of the laser ablation catheter embodiment of FIG. 1, the laser ablation catheter including an outer jacket which is operatively coupled to the laser ablation catheter.
Figure 3:
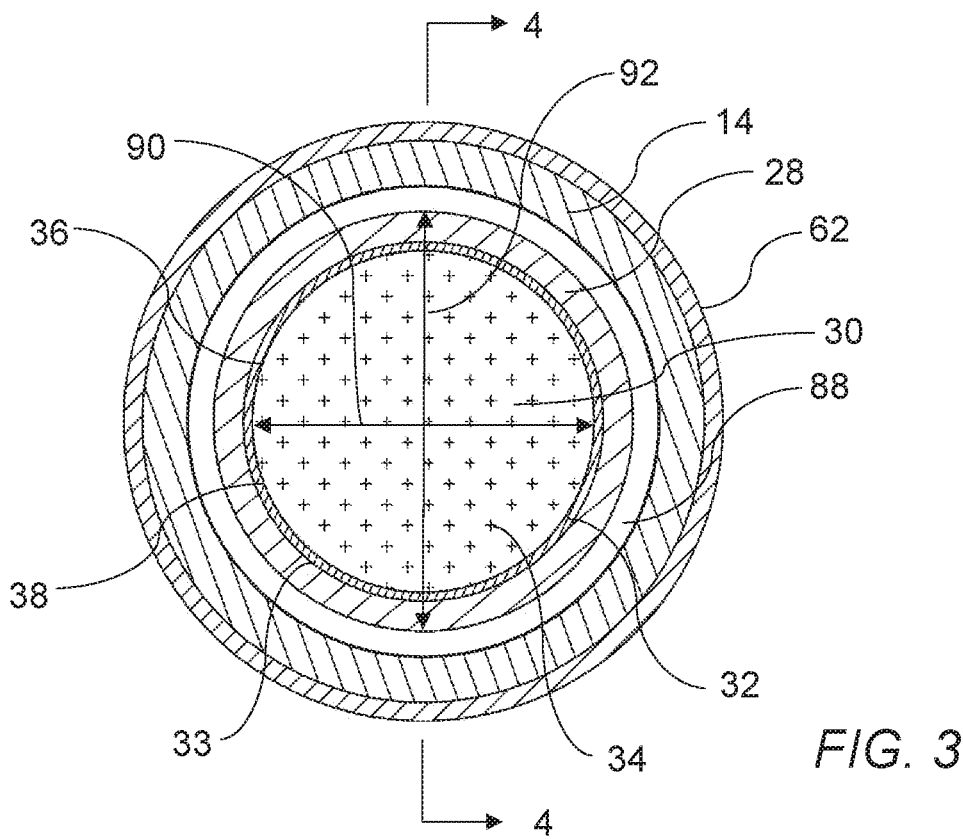
FIG. 3 is a transverse cross section view of the laser ablation catheter of FIG. 2 taken across lines 3-3 of FIG. 2.

An embodiment of an outer jacket 14 is shown in FIGS. 1 and 2. An inner surface 48 of the outer jacket embodiment 14 may be disposed over and secured relative to an outer surface 50 of the catheter tube 28. The outer jacket 14 may have a proximal end 52 that may be disposed at a proximal portion 54 of the catheter tube 28 and a distal end 56 that is disposed at an axial position 58 that is about 10 cm to about 60 cm proximal of the distal end 44 of the catheter tube 28. The outer jacket 14 may be secured relative to the catheter tube 28 such that the outer jacket 14 remains substantially fixed along a longitudinal axis 60 thereof relative to the catheter tube 28.

Some embodiments of an outer jacket 14 may include a radiopaque marker 62 which may be disposed at a distal portion 64 of the outer jacket 14. The radiopaque marker 62 may be configured to allow for the visualization of the distal end 56 of the outer jacket 14 through standard fluoroscopic imaging during a laser ablation catheter 12 procedure. In some cases, the radiopaque marker 62 may be configured as a tubular band which is secured such that it is proximal and substantially adjacent to the distal end 56 of the outer jacket 14. For some embodiments the radiopaque marker 62 may have an axial length 66 of about 1 mm to about 20 mm. The tubular band may be formed from any suitable radiopaque material such as platinum iridium, tungsten infused plastic, BaSO4 infused plastic, or the like.

Some outer jacket embodiments 14 may include an atraumatic radiopaque marker (not shown) wherein a material of a jacket body 68 is infused with a suitable radiopaque material. Such an atraumatic radiopaque marker may thus include an axial section of the jacket body which is disposed proximal and substantially adjacent to the distal end 56 of the outer jacket 14. For some embodiments, the atraumatic radiopaque marker may be infused with a radiopaque material such as barium sulfate, and may have an axial length of about 1 mm to about 20 mm.

Figure 8:
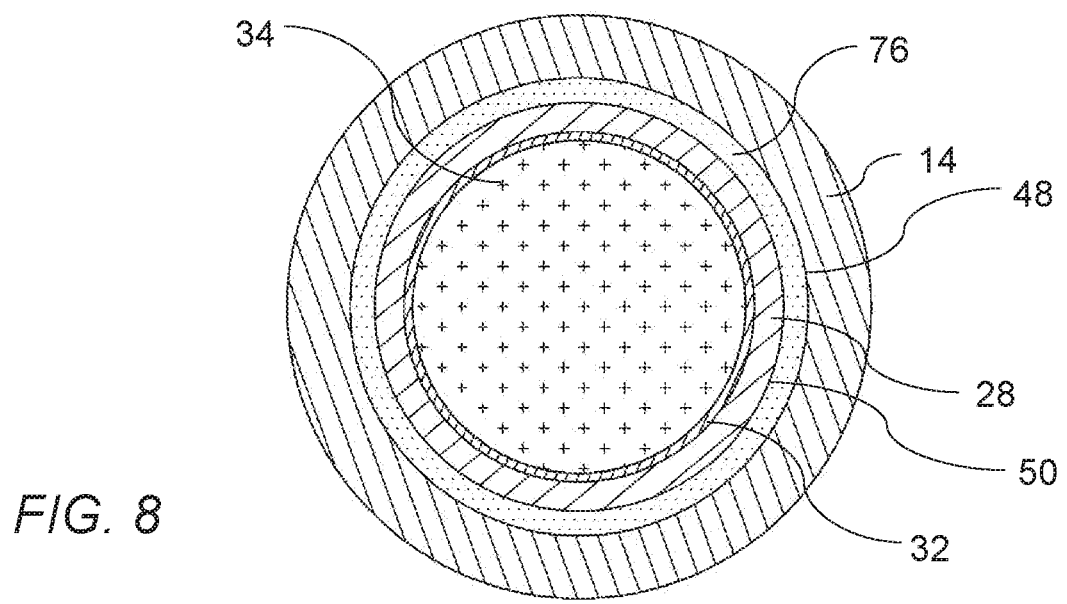
FIG. 8 is a transverse cross section view of the laser ablation catheter of FIG. 1 taken across lines 8-8 of FIG. 1.

In some cases, the catheter tube 28 may have an axial length 70 of about 180 cm to about 220 cm. The outer jacket 14 may have an axial length 72 of about 140 cm to about 180 cm. The outer jacket 14 may be secured relative to the catheter tube 28 such that the outer jacket 14 remains substantially fixed along a longitudinal axis 60 thereof relative to the catheter tube 28. A proximal portion 74 of the outer jacket 14 may be adhesively bonded to the catheter tube 28 (see FIG. 8) by applying an adhesive 76 between the inner surface 48 of the outer jacket 14 and the outer surface 50 of the catheter tube 28 thereby forming a proximal bond section 78.

In addition, the distal portion 64 of the outer jacket 14 may be adhesively bonded to the catheter tube 28 by applying an adhesive 76 between the inner surface 48 of the outer jacket 14 and the outer surface 50 of the catheter tube 28 thereby forming a distal bond section 79. Any suitable adhesive such as a cyanoacrylate, epoxy or the like may be used to create the proximal bond section 78 and the distal bond section 79. For some embodiments, an axial length 81 of the proximal bond section 78 may be about 0.039 inches to about 0.787 inches (see FIG. 10) and an axial length 80 of the distal bond section 79 may be about 0.039 inches to about 0.787 inches (see FIG. 4). Between the proximal bond section 78 and the distal bond section 79 the outer jacket 14 may be unbonded to the catheter tube 28 (see FIG. 5).

Some outer jacket embodiments 14 which are discussed herein may also include a manipulation section 49 which may include an axial section 51 of the outer jacket 14 which is disposed between the proximal portion 74 of the outer jacket 14 and a central portion 53 of the outer jacket 14. In some cases, the manipulation section 49 may represent the section of the outer jacket 14 which is most frequently manipulated/grasped by a user of the laser ablation catheter 12 while positioning and/or advancing the laser ablation catheter 12 during an ablation procedure (or any other suitable indication). In some cases, the manipulation section 49 may serve as a manual interface between the user and the laser ablation catheter 12. The manipulation section 49 may be configured to be crush resistant, kink resistant, and buckle resistant and may also be configured to have a longitudinal stiffness which is greater than the longitudinal stiffness of the respective portion of catheter tube 28 which is disposed within the manipulation section 49 of the outer jacket 14. For some embodiments, the manipulation section 49 may have a proximal terminus 55 (see FIG. 21) which is an axial distance 59 of about 5 cm to about 50 cm distal of the proximal end 52 (see FIG. 10) of the outer jacket 14, with the manipulation section 49 disposed distal to the proximal terminus 55. In some cases, the manipulation section may have an axial length 57 (see FIG. 21) of about 50 cm to about 150 cm. Any of the laser ablation catheter embodiments discussed herein may include a manipulation section thereof having any suitable feature, dimension or material of the manipulation section 49 of the outer jacket embodiments 14 discussed above.

The laser ablation catheter 12 may also include a connector strain relief 82, and a jacket strain relief 84. Connector strain relief embodiments 82 may be operatively coupled between the laser coupler 26 and jacket strain relief embodiments 84 and may be configured to protect the catheter tube 28 and waveguide from traumatic bending due to excessive axial loads. In turn the jacket strain 84 relief may be operatively coupled between the connector strain relief 82 and the outer jacket 14 and may be configured to protect the proximal portion 54 of the catheter tube 28 from traumatic bending due to excessive axial loads. The jacket strain relief 84 may be suitably secured to the connector strain relief 82 such that the jacket strain relief 84 remains fixed with respect to the connector strain relief 82. For example, the jacket strain relief 84 may be adhesively bonded to the connector strain relief 82 with a suitable adhesive such as cyanoacrylate or the like.

Figure 9:
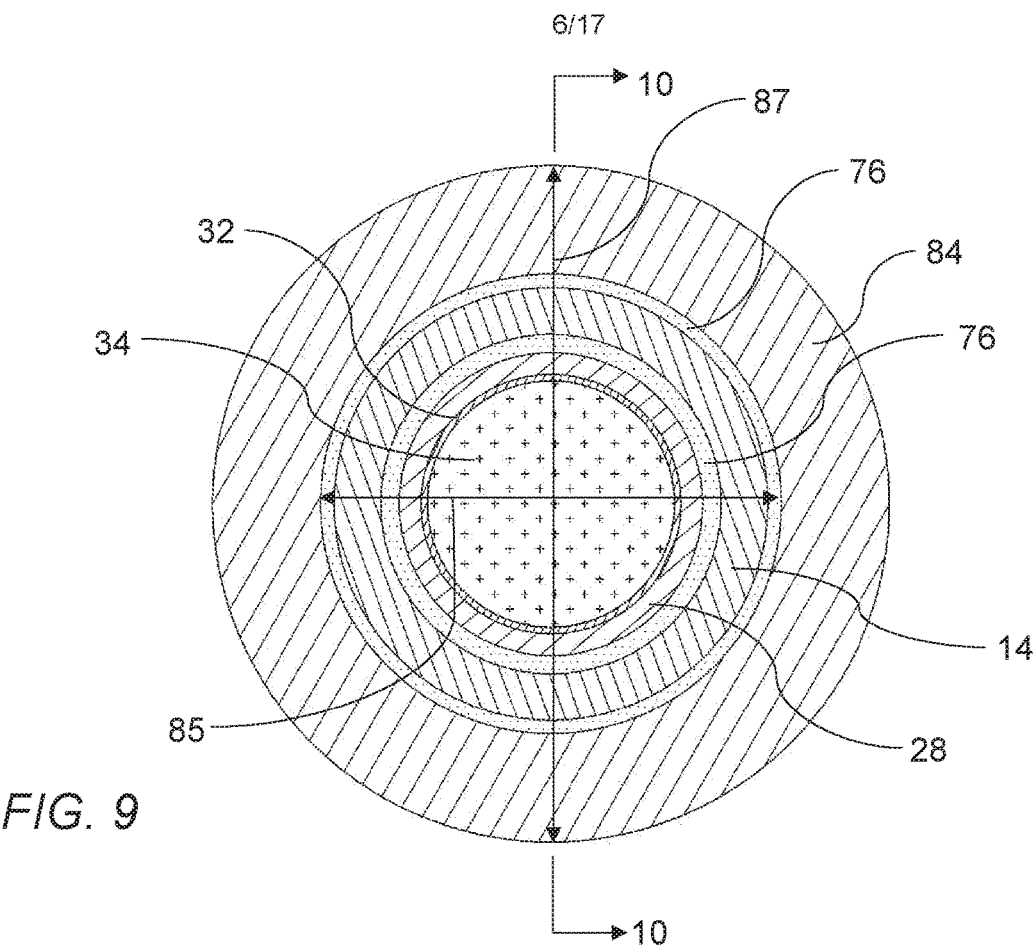
FIG. 9 is a transverse cross section view of the laser ablation catheter of FIG. 1 taken across lines 9-9 of FIG. 1.

For some embodiments, the jacket strain relief 84 may be monolithically formed from a suitable resilient polymer material such as Nylon® or Pebax®, silicone rubber, or the like. Alternatively, the jacket strain relief 84 may be formed from multiple layers of materials including Nylon® and Pebax®. For some embodiments the jacket strain relief 84 may have an inner diameter 85 of about 0.002 inches to about 0.004 inches larger than the outer diameter 92 of the catheter tube 28, and an outer diameter 87 of about 0.006 inches to about 0.050 inches larger than the outer diameter 92 of the catheter tube 28 (see FIG. 9). Some jacket strain relief embodiments 84 may have an axial length 86 of about 5 inches to about 20 inches.

Figure 6:
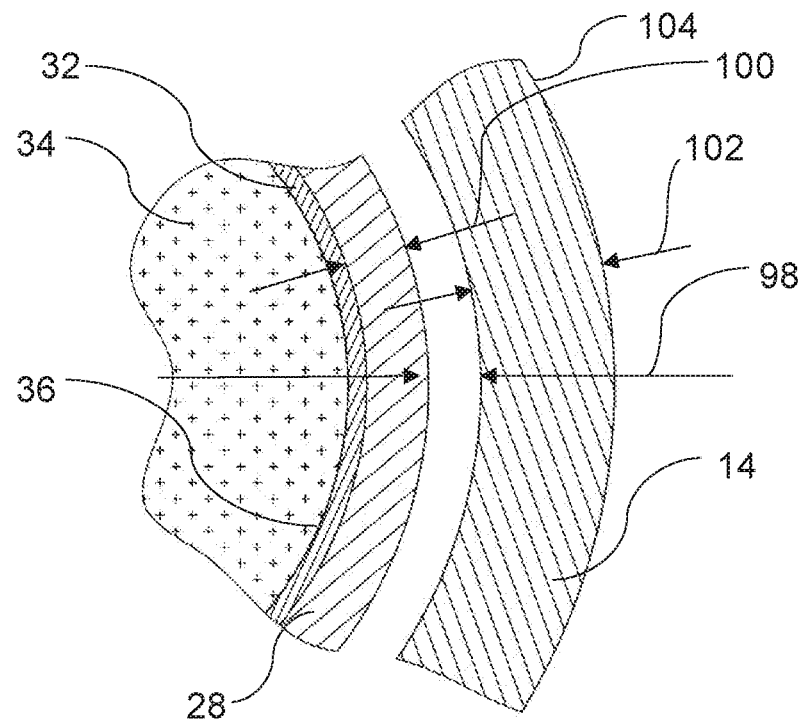
FIG. 6 is an enlarged view of the encircled section of the laser ablation catheter of FIG. 5.
Figure 7:
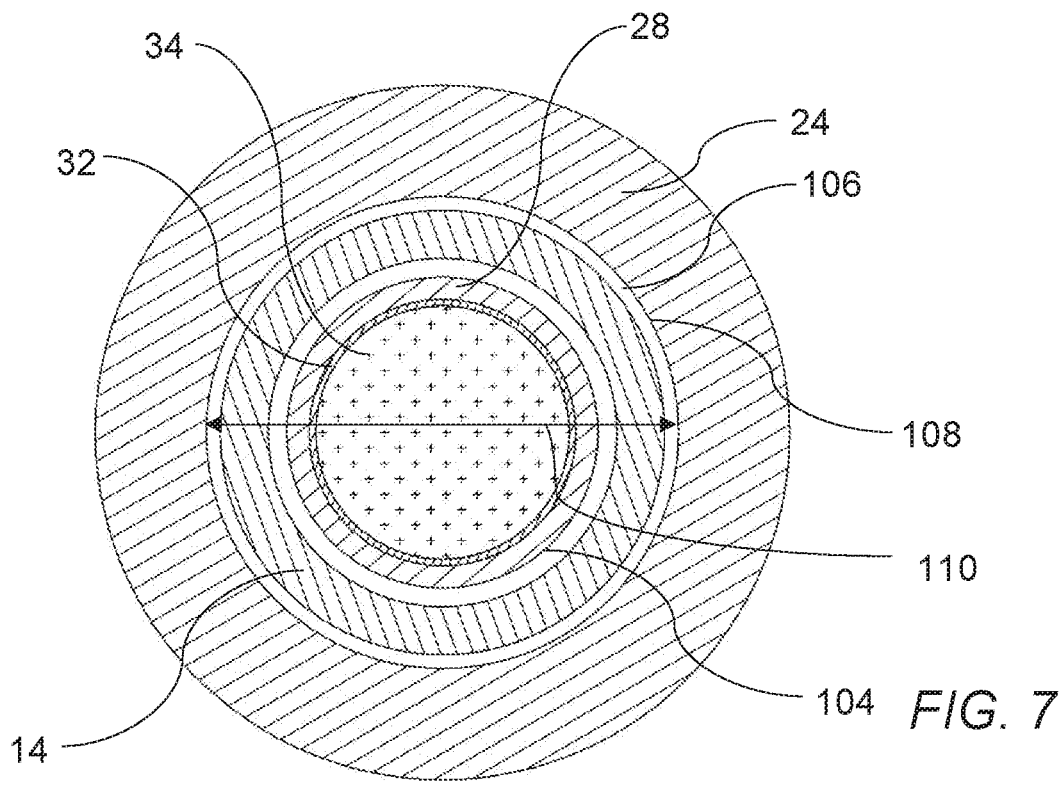
FIG. 7 is a transverse cross section view of the laser ablation catheter of FIG. 1 taken across lines 7-7 of FIG. 1.

In some cases, the outer jacket 14 may have a tubular configuration and may include an inner lumen 88 including the inner surface 48. As discussed above the inner lumen 88 of the outer jacket 14 may be configured to slide over the outer surface 50 of the catheter tube 28 with a close fit between the inner surface 48 of the outer jacket 14 and the outer surface 50 of the catheter tube 28. In some cases, embodiments of the catheter tube 28 may have an inner diameter 90 (diameter of inner surface) of about 0.042 inches to about 0.044 inches and an outer diameter (diameter of outer surface) of about 0.060 inches to about 0.062 inches. A respective outer jacket 14 may have an inner diameter 94 (diameter of inner surface) of about 0.042 inches to about 0.044 inches and an outer diameter 96 (diameter of outer surface) of about 0.060 inches to about 0.062 inches. In some cases, for laser ablation catheter embodiments 12 discussed herein the close fit between the outer surface 50 of the catheter tube 28 and the inner surface 48 of the inner lumen 88 of the outer jacket 14 may include a dimensional clearance 98 (see FIG. 6) of about 0.0005 inches to about 0.004 inches.

Some embodiments of the catheter tube 28 may have an inner diameter 90 of about 0.043 inches, an outer diameter 92 of about 0.061 inches, and a corresponding wall thickness 100 of about 0.009 inches. A respective outer jacket embodiment 14 may have an inner diameter 94 of about 0.062 inches, an outer diameter 96 of about 0.070 inches, and a corresponding wall thickness 102 of about 0.004 inches. Hence a ratio of the outer jacket wall thickness 102 to the catheter tube wall thickness 100 may be about 0.44. For some laser ablation catheter embodiments 12 discussed herein, the wall thickness 102 of the outer jacket 14 may be less than the wall thickness 100 of the catheter tube 28 generally such that the laser ablation catheter 12 maintains a relatively low profile along its axial length 70. In some cases, the ratio of the wall thickness 102 of the outer jacket 14 to the wall thickness 100 of the catheter tube 28 may be about 0.5 to about 0.9. For some outer jacket embodiments 14 discussed herein, an outer surface 104 of the outer jacket 14 may be configured to easily slide into an inner lumen 106 of the support catheter 24, with the inner lumen 106 of the support catheter 24 having an inner surface 108 with a diameter 110 that is at most one French (⅓ mm) size larger than the outer diameter 92 of the outer surface 50 of the catheter tube 28. Despite having a thinner wall thickness 102 relative to a wall thickness 100 of the catheter tube 28, the outer jacket 14 may still be configured such that it provides axial stiffness and crush resistance to the laser ablation catheter 12 that is sufficient for typical manipulation by a user without being crushed, kinked, or otherwise distorted.

The outer jacket 14 may include the tubular jacket body 68 that has a longitudinal stiffness greater than a longitudinal stiffness of the catheter tube 28 at the proximal portion 54 of the catheter tube 28. The longitudinal stiffness of the outer jacket 14 may be made greater than the longitudinal stiffness of the catheter tube 28 in some cases by inserting structural reinforcement into the jacket body 68, by utilizing a jacket body 68 material that has a high flexural modulus, or by incorporating an increased wall thickness into a proximal portion 74 of the jacket body 68. All of these features of outer jacket 14 may also act to increase the crush resistance of the outer jacket 14 when a radial load is applied to the outer jacket 14 by a user. FIGS. 15-35 depict outer jacket embodiments wherein at least one of these features has been incorporated into the outer jacket embodiment, with any possible combination of the jacket body the features which increase the longitudinal stiffness and crush resistance of the jacket body being contemplated herein. Each of the outer jacket embodiments depicted in FIGS. 15-35 and discussed herein may be configured as has been previously discussed for outer jacket 14 which is depicted in FIGS. 1-9.

An embodiment an outer jacket 112 having a tubular reinforcement 114 that is crush resistant and that is disposed along a tubular jacket body 116 is depicted in FIGS. 15-18. The outer jacket 112 may have a proximal end 113 that may be disposed at a proximal portion 54 of the catheter tube 28 of a respective laser ablation catheter embodiment and a distal end 115 that may be disposed at an axial position 58 that is about 10 cm to about 60 cm proximal of the distal end 44 of the catheter tube 28 (see FIG. 2). The outer jacket 112 may be secured relative to the catheter tube 28 such that the outer jacket 112 remains substantially fixed along a longitudinal axis 60 thereof relative to the catheter tube 28.

In some cases, the tubular reinforcement 114 may act to increase the hoop strength of the respective outer jacket 112. As discussed above, the jacket body 116 and tubular reinforcement 114 may also be configured in dimensions, materials, and features that increase the longitudinal stiffness and crush resistance of a respective laser ablation catheter embodiment (such as the laser ablation catheter 12). For example, laser ablation catheter 12 may include outer jacket embodiment 112 as a replacement for outer jacket embodiment 14. Embodiments of tubular reinforcements are shown in FIGS. 11-14. Some embodiments of tubular reinforcements may include coils or braids which provide axial stiffness and crush resistance to the outer jacket, while still allowing for flexibility of the outer jacket and respective laser ablation catheter during an ablation procedure.

Figure 15:
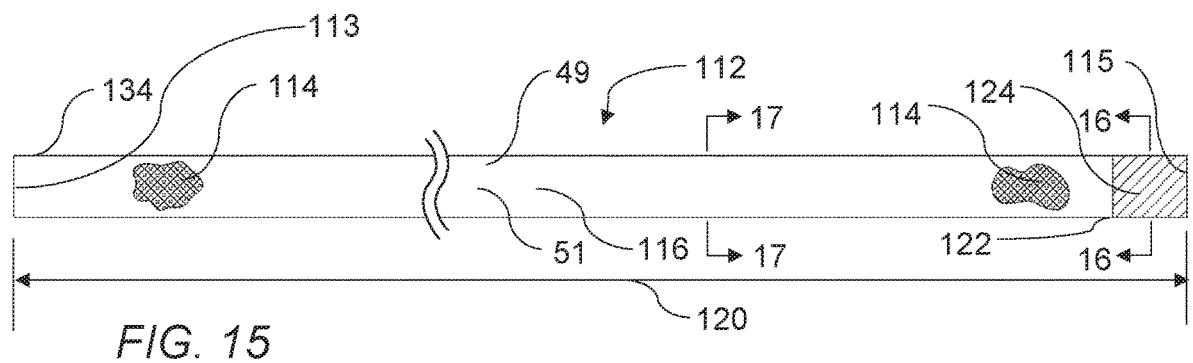
FIG. 15 is an elevation view of an outer jacket embodiment having a substantially constant transverse outer dimension and including a tubular reinforcement embodiment.
Figure 16:
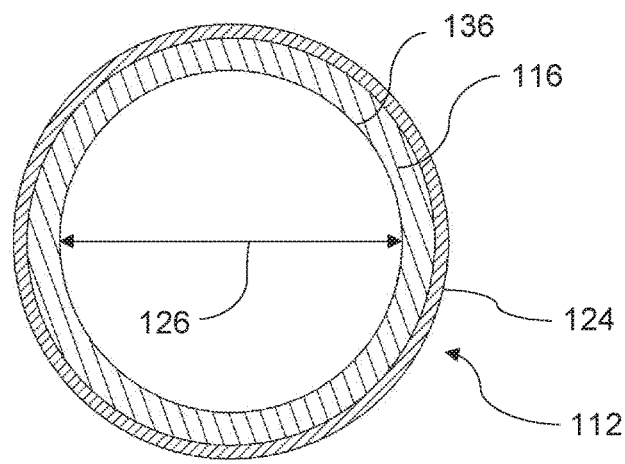
FIG. 16 is a transverse cross section view of the outer jacket embodiment of FIG. 15 taken along lines 16-16 of FIG. 15.
Figure 17:
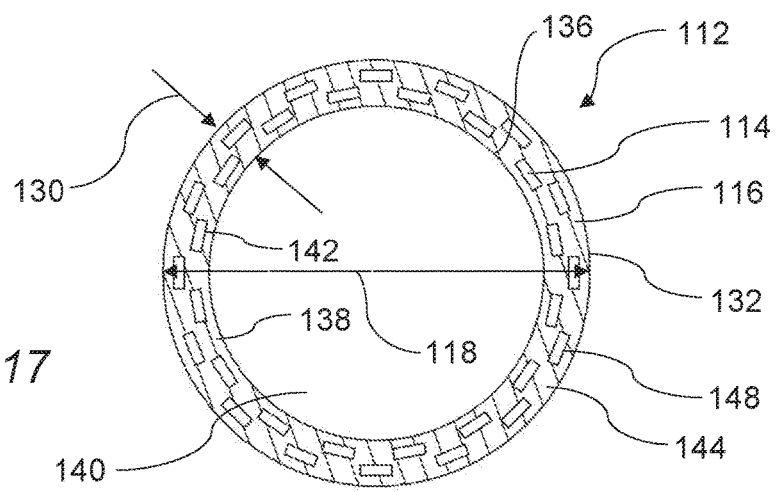
FIG. 17 is a transverse cross section view of the outer jacket embodiment of FIG. 15 taken along lines 17-17 of FIG. 15.

The outer jacket embodiment 112 may have a substantially constant transverse outer dimension 118, and may have an axial length 120 (as shown in FIG. 15) of about 140 cm to about 180 cm. A distal portion 122 of the outer jacket may include a radiopaque marker 124, the radiopaque marker 124 having any suitable feature, dimension, or material of any of the radiopaque marker embodiments discussed herein. As discussed above, embodiments of the catheter tube 28 may have an inner diameter 90 of about 0.043 inches, an outer diameter 92 of about 0.061 inches, and a corresponding wall thickness 100 of about 0.009 inches. Embodiments of the outer jacket 112 may have an inner diameter 126 of about 0.062 inches, an outer diameter 118 of about 0.070 inches, and a corresponding wall thickness 130 of about 0.004 inches. Hence a ratio of the outer jacket 112 wall thickness 130 to a wall thickness 100 of the catheter tube 28 may be about 0.44 for some embodiments. In some cases, the ratio of the wall thickness 130 of the outer jacket 112 to the wall thickness 100 of the catheter tube 28 may be about 0.5 to about 0.9.

An outer surface 132 of the outer jacket 112 may be configured to easily slide into the inner lumen 106 of the support catheter 24, with the inner lumen 106 of the support catheter 24 including the inner surface 108 having a diameter 110 that is at most one French larger than the diameter 92 of the outer surface 50 of the catheter tube 28. Despite having a thinner wall thickness 130 relative to a wall thickness 100 of the catheter tube 28, the outer jacket 112 may still be configured such that it provides axial stiffness and crush resistance to the laser ablation catheter embodiment 12.

Figure 4:
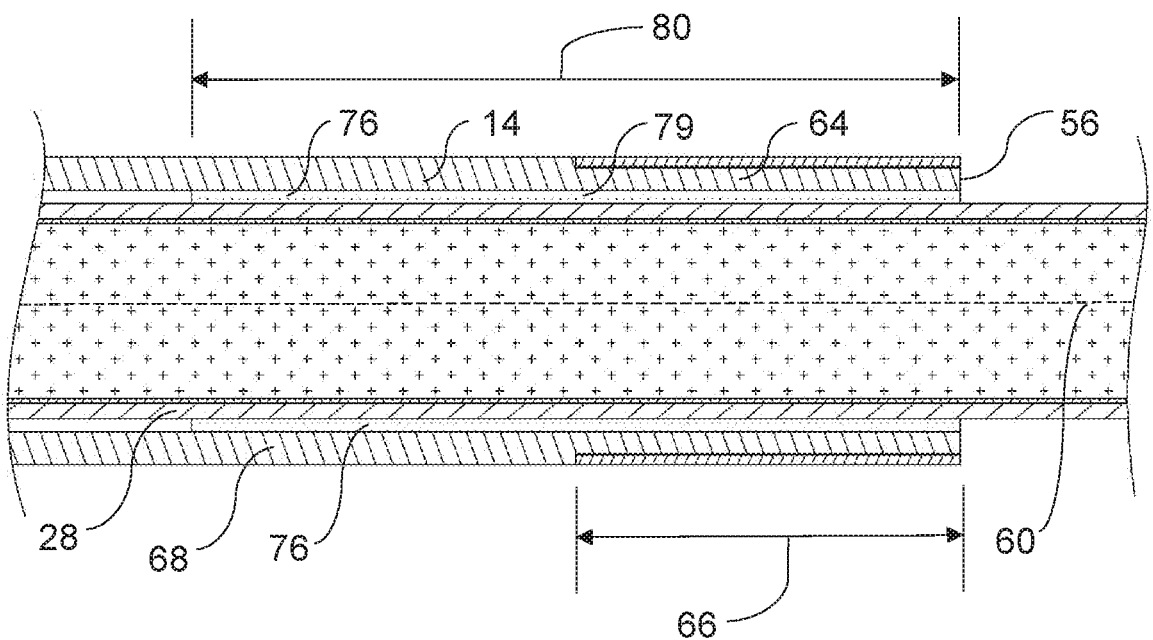
FIG. 4 is a transverse sectional view of the laser ablation catheter of FIG. 2 taken across lines 4-4 of FIG. 3.
Figure 10:
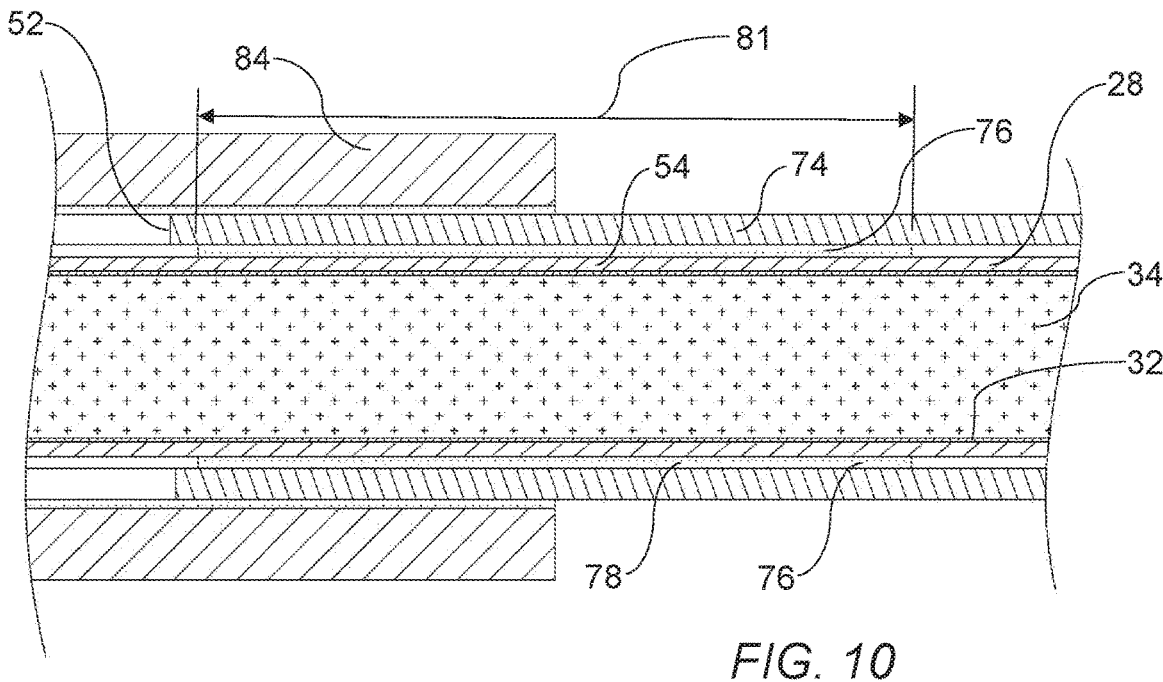
FIG. 10 is a transverse cross section view of the laser ablation catheter embodiment of FIG. 2 taken across lines 10-10 of FIG. 9.

The outer jacket 112 may be secured relative to the catheter tube 28 such that the outer jacket 112 remains substantially fixed along the longitudinal axis 60 of the catheter tube 28. A proximal portion of the outer jacket 134 may be adhesively bonded to the catheter tube 28 (see FIG. 8 for reference) by applying adhesive 76 between an inner surface 136 of the outer jacket 112 and the outer surface 50 of the catheter tube 28 thereby forming a proximal bond section (which may be the same as or similar to proximal bond section 78 which is depicted in FIG. 10). In addition, the distal portion 122 of the outer jacket 112 may be adhesively bonded to the catheter tube 28 by applying adhesive 76 between the inner surface 136 of the outer jacket 112 and the outer surface 50 of the catheter tube 28 thereby forming a distal bond section (which may be the same as or similar to distal bond section 79 which is depicted in FIG. 4). Any suitable adhesive 76 such as a cyanoacrylate, epoxy or the like may be used to create the proximal bond section and the distal bond section. For some embodiments, an axial length of the proximal bond section may be about 0.039 inches to about 0.787 inches and an axial length of the distal bond section may be about 0.039 inches to about 0.787 inches. Between the proximal bond section and the distal bond section the outer jacket 112 may be unbonded to the catheter tube 28 (see FIG. 5 wherein outer jacket embodiment 14 is similarly unbonded to the catheter tube 28).

The outer jacket 112 may include the tubular jacket body 116 that has a longitudinal stiffness which may be greater than a longitudinal stiffness of the catheter tube 28 at the proximal portion 54 of the catheter tube 28. The longitudinal stiffness of the outer jacket 112 may be made greater than the longitudinal stiffness of the catheter tube 28 via the addition of the tubular reinforcement 114. In some cases, the tubular reinforcement 114 may be disposed between layers of jacket body 116 materials of the outer jacket embodiment 112. The jacket body 116 may include a tubular inner jacket layer 138 having an inner lumen 140 which may be configured to slide over the catheter tube 28 with a close fit therebetween, and with the tubular reinforcement 114 being disposed on an outer surface 142 of the inner jacket layer 138. A tubular outer jacket layer 144 having an inner lumen with interior surface 148 may in turn be disposed over and cover the tubular reinforcement 114. In some cases, the inner jacket layer 138 and the outer jacket layer 144 may be formed from the same material. For some embodiments portions of the inner jacket layer 138 may be thermally fused or adhesively bonded to respective portions of the outer jacket layer 144. Thus, the tubular reinforcement 114 may be enclosed by jacket body 116 material.

FIG. 11 depicts an embodiment of a tubular reinforcement 150 which is configured as a reinforcement wire 152 which is formed into a tubular coil 154, with the reinforcement wire 152 having a substantially round transverse cross section for the embodiment shown. For some embodiments, a diameter 156 of the reinforcement wire 152 may be about 0.0005 inches to about 0.01 inches (see FIG. 11A). The tubular coil 154 may have a coil inner diameter 158 of about 0.002 inches to about 0.004 inches larger than the outer diameter 92 of the catheter tube 28. The reinforcement wire 152 may be formed from any suitable high strength, flexible and/or resilient material, for example the reinforcement wire 152 could be formed from a metal such as stainless steel or a polymer such as polycarbonate. For some embodiments the reinforcement wire 152 may be formed from Kevlar® para-aramid synthetic fiber material or from any suitable natural protein fiber such as silk.

FIG. 12 depicts an embodiment of a tubular reinforcement 160 which is configured as a reinforcement ribbon 162 which is formed into a tubular coil 164, with the reinforcement ribbon 162 having a substantially rectangular transverse cross section. For some embodiments a thickness 166 of the reinforcement ribbon 162 may be from about 0.0005 inches to about 0.10 inches and a width 168 of the reinforcement ribbon 162 may be from about 0.002 inches to about 0.005 inches (see FIG. 12A). The tubular coil 164 may have a coil inner diameter 170 of about 0.002 inches to about 0.004 inches larger than the outer diameter 92 of the catheter tube 28. The reinforcement ribbon 162 may be formed from any suitable flexible resilient material, for example the reinforcement ribbon 162 could be formed from a metal such as stainless steel or a polymer such as polycarbonate. For some embodiments the reinforcement ribbon 162 may be formed from Kevlar® para-aramid synthetic fiber material or from any suitable natural protein fiber such as silk.

FIG. 13 depicts an embodiment of a tubular reinforcement 172 which is configured as a plurality of reinforcement ribbons 174 which are woven together into a tubular braid 176. In some instances, each reinforcement ribbon 174 may have a substantially rectangular transverse cross section. For some embodiments a thickness 178 of each reinforcement ribbon 174 may be from about 0.0005 inches to about 0.010 inches, and a width 180 of each reinforcement ribbon 174 may be from about 0.002 inches to about 0.005 inches (see FIG. 14A). For some embodiments, the tubular braid 176 may have a braid inner diameter 182 of about 0.002 inches larger to about 0.004 inches larger than the outer diameter 92 of the catheter tube 28. The reinforcement ribbon 174 may be formed from any suitable flexible resilient material, for example the reinforcement ribbon 174 could be formed from a metal such as stainless steel or a polymer such as polycarbonate. For some embodiments the reinforcement ribbon 174 may be formed from Kevlar® para-aramid synthetic fiber material or from any suitable natural protein fiber such as silk.

Some embodiments of a tubular reinforcement may be configured similarly to tubular reinforcement 172 but including a plurality of reinforcement wires having a substantially round transverse cross section formed into a braided structure. For some such embodiments, a diameter each reinforcement wire may be from about 0.0005 inches to about 0.01 inches. The corresponding tubular braid may have a braid inner diameter of about 0.002 inches to about 0.004 inches larger than the outer diameter 92 of the catheter tube 28. The reinforcement wire embodiments may be formed from any suitable flexible resilient material, for example the reinforcement wire could be formed from a metal such as stainless steel or any suitable polymer. For some embodiments the reinforcement wire may be formed from Kevlar® para-aramid synthetic fiber material or from any suitable natural protein fiber such as silk.

In some cases, it may be useful to configure outer jacket embodiments such that certain proximal axial sections of the outer jacket embodiment have increased longitudinal stiffness and crush resistance as compared to distal axial sections of the outer jacket. During an ablation procedure, a user of the laser ablation catheter 12 may typically manipulate the laser ablation catheter 12 by grasping proximal portions of the laser ablation catheter 12 during which time radial and axial loads are applied to the laser ablation catheter 12. At the same time, distal portions of the laser ablation catheter 12 may need to remain flexible in order to negotiate potential tortuous paths within a patient or any other suitable indication.

Figure 18:
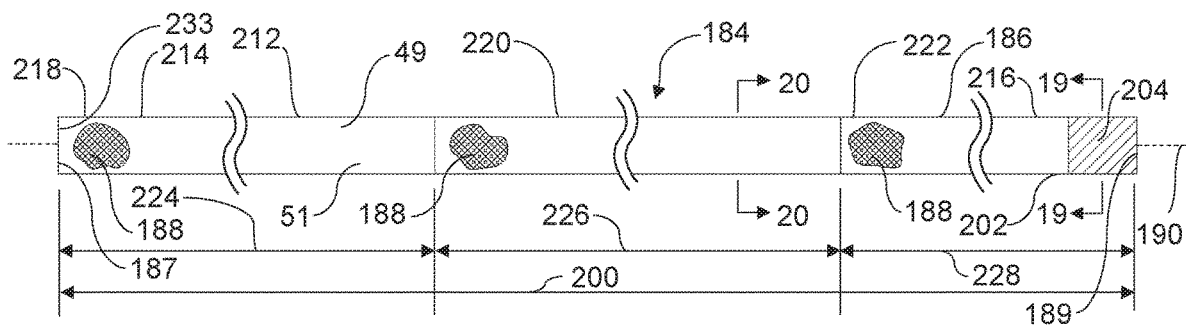
FIG. 18 is an elevation view of an outer jacket embodiment having a substantially constant transverse outer dimension and including a tubular reinforcement and a plurality of axial sections.
Figure 19:
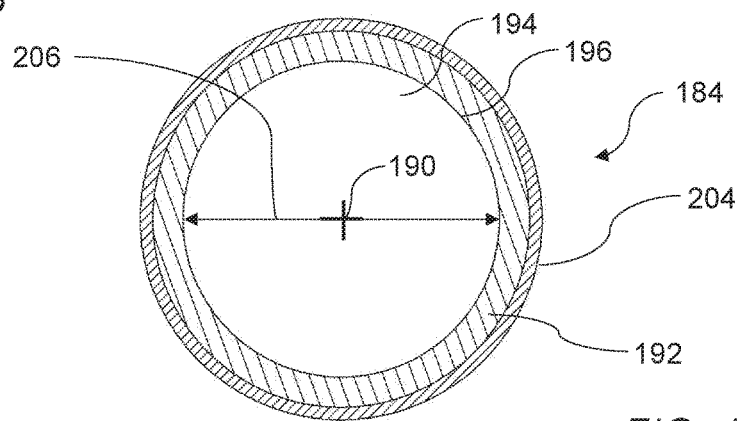
FIG. 19 is a transverse cross section view of the outer jacket embodiment of FIG. 18 taken along lines 19-19 of FIG. 18.
Figure 20:
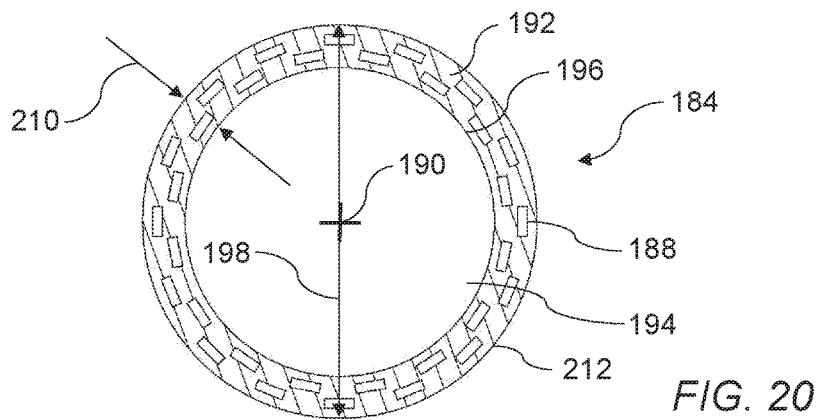
FIG. 20 is a transverse cross section view of the outer jacket embodiment of FIG. 18 taken along lines 20-20 of FIG. 18.

An embodiment of an outer jacket 184 having multiple axial sections 186 each of which includes a tubular reinforcement 188 is shown in FIGS. 18-20. The outer jacket 184 may have a proximal end 187 that may be disposed at a proximal portion 54 of the catheter tube 28 of a respective laser ablation catheter embodiment and a distal end 189 that may be disposed at an axial position 58 that is about 10 cm to about 60 cm proximal of the distal end 44 of the catheter tube 28 (see FIG. 2). The outer jacket 184 may be secured relative to the catheter tube 28 such that the outer jacket 184 remains substantially fixed along a longitudinal axis 60 thereof relative to the catheter tube 28.

The outer jacket 184 may include a plurality of sequential axial sections 186 which are longitudinally disposed along a longitudinal axis 190 of the outer jacket 184 with each axial section 186 including a material having a flexural modulus which is different than the flexural moduli of respective adjacent axial section 186 materials. In some cases, the flexural modulus of each material of each respective sequential axial section 186 may decrease distally along the outer jacket. The tubular reinforcement 188 may be disposed along a tubular jacket body 192, each of which may be configured in dimension, material(s) etc. to increase the longitudinal stiffness and crush resistance of a respective laser ablation catheter embodiment (such as the laser ablation catheter 12). For example, laser ablation catheter embodiment 12 may include the outer jacket embodiment 184 which would replace outer jacket embodiment 14 discussed above.

The outer jacket 184 may include an inner lumen 194 having an inner surface 196 which may be configured to slide over the outer surface 50 of the catheter tube 28 with a close fit (see FIG. 6) between the inner surface 196 and the outer surface 50. In some cases, the close fit between the outer surface 50 of the catheter tube 28 and the inner surface 196 of the inner lumen 194 of the outer jacket 184 includes a dimensional clearance (see FIG. 6) of about 0.0005 inches to about 0.004 inches. The outer jacket embodiment 184 which is depicted in FIG. 18 may have a substantially constant transverse outer dimension 198, and may have an axial length 200 of about 140 cm to about 180 cm. A distal portion 202 of the outer jacket 184 may include with a radiopaque marker 204, with the radiopaque marker 204 having any suitable feature, dimension or material of any of the radiopaque marker embodiments discussed herein.

Embodiments of the catheter tube 28 may have an inner diameter 90 of about 0.043 inches, an outer diameter 92 of about 0.061 inches, and a corresponding wall thickness 100 of about 0.009 inches. The outer jacket embodiment 184 may have an inner diameter 206 of about 0.062 inches, an outer diameter 198 of about 0.070 inches, and a corresponding wall thickness 210 of about 0.004 inches. Hence a ratio of the wall thickness 210 of the outer jacket 184 to a wall thickness 100 of the catheter tube 28 may be about 0.44. In some cases, the ratio of the wall thickness 210 of the outer jacket 184 to the wall thickness 100 of the catheter tube 28 may be about 0.5 to about 0.9.

For some embodiments, an outer surface 212 of the outer jacket 184 may be configured to easily slide into the inner lumen 106 of the support catheter 24, with the inner lumen 106 of the support catheter 24 having the inner surface 108 with diameter 110 that is at most one French larger than the diameter 92 of the outer surface 50 of the catheter tube 28. Despite having a thinner wall thickness 210 relative to a wall thickness 100 of the catheter tube 28, the outer jacket 184 may still be configured such that it provides axial stiffness and crush resistance to the laser ablation catheter 12 that is sufficient for typical manipulation by a user without being crushed, kinked or otherwise distorted.

The outer jacket embodiment 184 may be secured relative to the catheter tube 28 such that the outer jacket 184 remains substantially fixed along a longitudinal axis 60 thereof relative to the catheter tube 28. A proximal portion 214 of the outer jacket 184 may be adhesively bonded to the catheter tube 28 (see FIG. 8 for reference) by applying an adhesive 76 between the inner surface 196 of the outer jacket 184 and the outer surface 50 of the catheter tube 28 thereby forming a proximal bond section (which may be the same as or similar to the proximal bond section 78 which is depicted in FIG. 10). In addition, a distal portion 216 of the outer jacket 184 may be adhesively bonded to the catheter tube 28 by applying an adhesive 76 between the inner surface 196 of the outer jacket 184 and the outer surface 50 of the catheter tube 28 thereby forming a distal bond section (which may be the same as or similar to the distal bond section 79 which is depicted in FIG. 4). Any suitable adhesive 76 such as a cyanoacrylate, epoxy or the like may be used to create the proximal bond section and the distal bond section. For some embodiments, an axial length of the proximal bond section may be about 0.039 inches to about 0.787 inches and an axial length of the distal bond section may be about 0.039 inches to about 0.787 inches. Between the proximal bond section and the distal bond section the outer jacket 184 may be unbonded to the catheter tube 28 (see FIG. 5 wherein outer jacket embodiment 14 is similarly unbonded to the catheter tube 28).

The outer jacket 184 includes the tubular jacket body 192 which includes the plurality of axial sections 186. Some proximal portions 214 of the tubular jacket body 192 (and any respective axial sections 184 disposed therein) may have a longitudinal stiffness which greater than a longitudinal stiffness of the catheter tube 28 at a proximal portion 54 of the catheter tube 28. The longitudinal stiffness of the outer jacket 184 may be made greater than the longitudinal stiffness of the catheter tube 28 in some axial sections 186 via the addition of the tubular reinforcement 188 and via variation of the flexural modulus of the materials of those axial sections 186.

In some cases, each axial section 186 may be secured to a respective adjacent axial section 186 such as by thermal fusion thereby securing each axial section 186 to the respective adjacent axial section 186. Each axial section 186 of the outer jacket embodiment 184 may be configured with a tubular reinforcement 188 as has been previously discussed wherein the tubular reinforcement 188 may be disposed between layers of jacket body 192 materials.

For some embodiments, referring to FIG. 18, a first material of a respective first axial section 218 may include a material such as Nylon® 12, a second material of a respective second axial section 220 may include a material such as Pebax® 4033, and a third material of a respective third axial section 222 may include a material such as Pebax® 3533. Nylon® 12 may have a flexural modulus of about 1.5 GPa to about 1.7 GPa and is manufactured by EMS-Chemie Inc., 2060 Corporate way, PO Box 1717, Sumpter, S.C., U.S.A. Pebax® 4033 may have a flexural modulus of about 0.07 GPa to about 0.009 GPa and is manufactured by Arkema Group, 420 Rue d' Estienne d' Orves, 92705, Columbes redex, France. Pebax® 3533 may have a flexural modulus of about 0.02 GPa to about 0.022 GPa. In this case, the flexural modulus of Pebax® 4033 is lower than the flexural modulus of Nylon® 12, and the flexural modulus of Pebax® 3533 is lower than the flexural modulus of Pebax® 4033.

As such, the first axial section 218 is the proximal most axial section and includes the material having the highest flexural modulus of the three axial sections 218, 220, and 222. A distal end of the first axial section 218 is secured to a proximal end of the second axial section. The second axial section 220 is disposed axially between the first axial section 218 and the third axial section 222. The second axial section 220 includes a material having a flexural modulus which is lower than a flexural modulus of the material of the first axial section 218 and higher than a flexural modulus of a material of the third axial section 222. A distal end of the second axial section 220 is secured to a proximal end of the third axial section 222. For this embodiment, the flexural modulus of the materials of the respective axial sections 218, 220, and 222 decreases distally along the outer jacket embodiment 184. In some cases, an axial length 224 of the first axial section 218 may be from about 140 cm to about 160 cm, an axial length 226 of the second axial section 220 may be from about 5 mm to about 15 mm, and an axial length 228 of the third axial section 222 may be from about 2 mm to about 5 mm.

Figure 21:
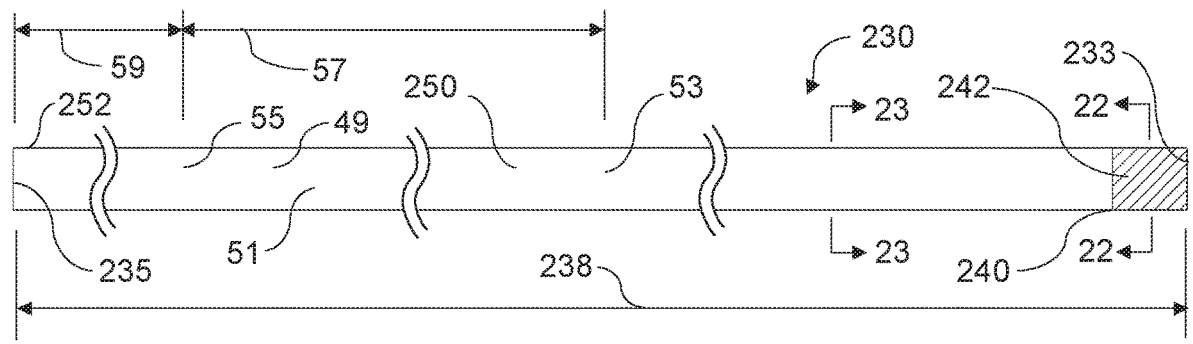
FIG. 21 is an elevation view of an outer jacket embodiment having a substantially constant transverse outer dimension and which includes a plurality of axial sections.
Figure 22:
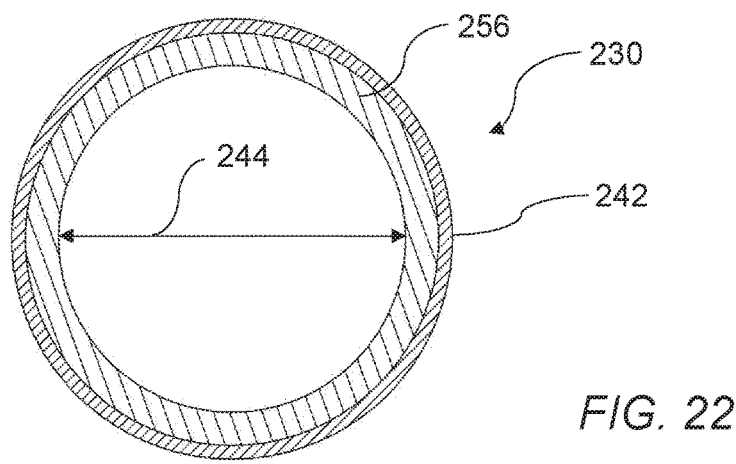
FIG. 22 is a transverse cross section view of the outer jacket embodiment of FIG. 21 taken along lines 21-21 of FIG. 20.
Figure 23:
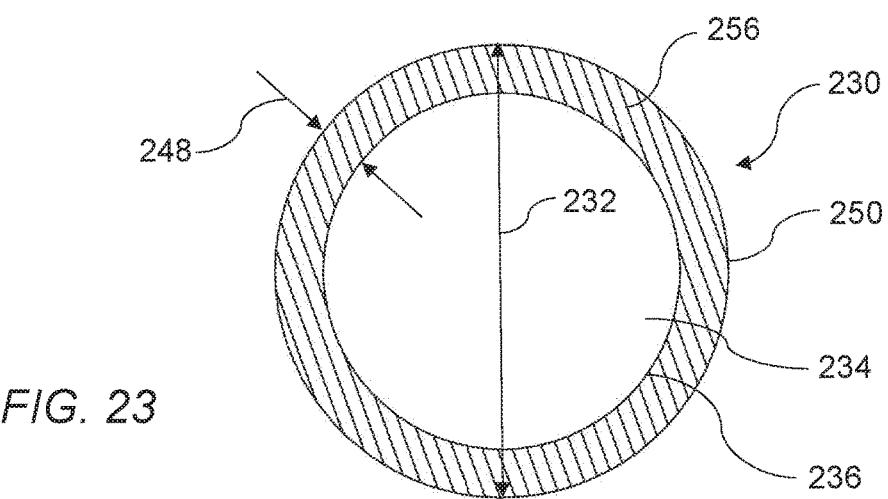
FIG. 23 is a transverse cross section view of the outer jacket embodiment of FIG. 21 taken along lines 23-23 of FIG. 21.

For some outer jacket embodiments, the outer diameter of the jacket body may be minimized such that the respective laser ablation catheter may easily fit into an accessory catheter such as a support catheter. For this reason, it may be useful to form an outer jacket from a single material. In some cases the material of the outer jacket may be any suitable polymer such as Nylon® 12. The outer jacket 230 which is depicted in FIGS. 21-23 may be monolithically formed from a single material. The outer jacket 230 may have a proximal end 233 that may be disposed at a proximal portion 54 of the catheter tube 28 of a respective laser ablation catheter embodiment and a distal end 235 that may be disposed at an axial position 58 that is about 10 cm to about 60 cm proximal of the distal end 44 of the catheter tube 28 (see FIG. 2). The outer jacket 230 may be secured relative to the catheter tube 28 such that the outer jacket 230 remains substantially fixed along a longitudinal axis 60 thereof relative to the catheter tube 28.

The outer jacket 230 may have tubular configuration may be configured with a substantially constant transverse outer dimension 232. A respective laser ablation catheter embodiment (such as the laser ablation catheter 12) may be configured to include the outer jacket embodiment 112 (which would replace outer jacket embodiment 14). The outer jacket 230 may include an inner lumen 234 having an inner surface 236 which may be configured to slide over the outer surface 50 of the catheter tube 28 with a close fit between the inner surface 236 and the outer surface 50. In some cases the close fit between the outer surface 50 of the catheter tube 28 and the inner surface 236 of the inner lumen 234 of the outer jacket 230 includes a dimensional clearance (see FIG. 6) of about 0.0005 inches to about 0.004 inches.

The outer jacket embodiment 230 which is depicted in FIG. 21 may have the substantially constant transverse outer dimension 232 and may have an axial length 238 (as shown in FIG. 21) of about 140 cm to about 180 cm. A distal portion 240 of the outer jacket 230 may include a radiopaque marker 242 which may have any suitable feature, dimension or material as any of the radiopaque marker embodiments which are discussed herein. Some catheter tube embodiments 28 may have an inner diameter 90 of about 0.043 inches, an outer diameter 92 of about 0.061 inches, and a corresponding wall thickness 100 of about 0.009 inches. The outer jacket embodiment 230 may have an inner diameter 244 of about 0.062 inches, an outer diameter 232 of about 0.070 inches, and a corresponding wall thickness 248 of about 0.004 inches. Hence a ratio of the outer jacket 230 wall thickness 248 to the wall thickness 100 may of the catheter tube 28 be about 0.44. In some cases, the ratio of the wall thickness 248 of the outer jacket 230 to the wall thickness 100 of the catheter tube 28 may be about 0.5 to about 0.9.

An outer surface 250 of the outer jacket 230 may be configured and sized generally to easily slide into the inner lumen 106 of the support catheter 24, with the inner lumen 106 of the support catheter 24 having an inner surface 108 with a diameter 110 that is at most one French larger than the diameter 92 of the outer surface 50 of the catheter tube 28. Despite having a thinner wall thickness 248 relative to a wall thickness 100 of the catheter tube 28, the outer jacket 230 may still be configured such that it provides axial stiffness and crush resistance to the laser ablation catheter 12 that is sufficient for typical manipulation by a user without being crushed, kinked or otherwise distorted to an extent that performance of the laser ablation catheter may be reduced.

The outer jacket embodiment 230 may be secured relative to the catheter tube 28 such that the outer jacket 230 remains substantially fixed along a longitudinal axis 60 of the catheter tube 28. A proximal portion 252 of the outer jacket 252 may be adhesively bonded to the catheter tube 28 (see FIG. 8 for reference) by applying an adhesive 76 between the inner surface 236 of the outer jacket 230 and the outer surface 50 of the catheter tube 28 thereby forming a proximal bond section (which may be the same as or similar to proximal bond section 78 which is depicted in FIG. 10). In addition, a distal portion 240 of the outer jacket 230 may be adhesively bonded to the catheter tube 28 by applying an adhesive 76 between the inner surface 236 of the outer jacket 230 and the outer surface 50 of the catheter tube 28 thereby forming a distal bond section (which may be the same as or similar to distal bond section 79 which is depicted in FIG.

4). Any suitable adhesive 76 such as a cyanoacrylate, epoxy or the like may be used to create the proximal bond section and the distal bond section. For some embodiments, an axial length of the proximal bond section may be about 0.039 inches to about 0.787 inches and an axial length of the distal bond section may be about 0.039 inches to about 0.787 inches.

Figure 5:
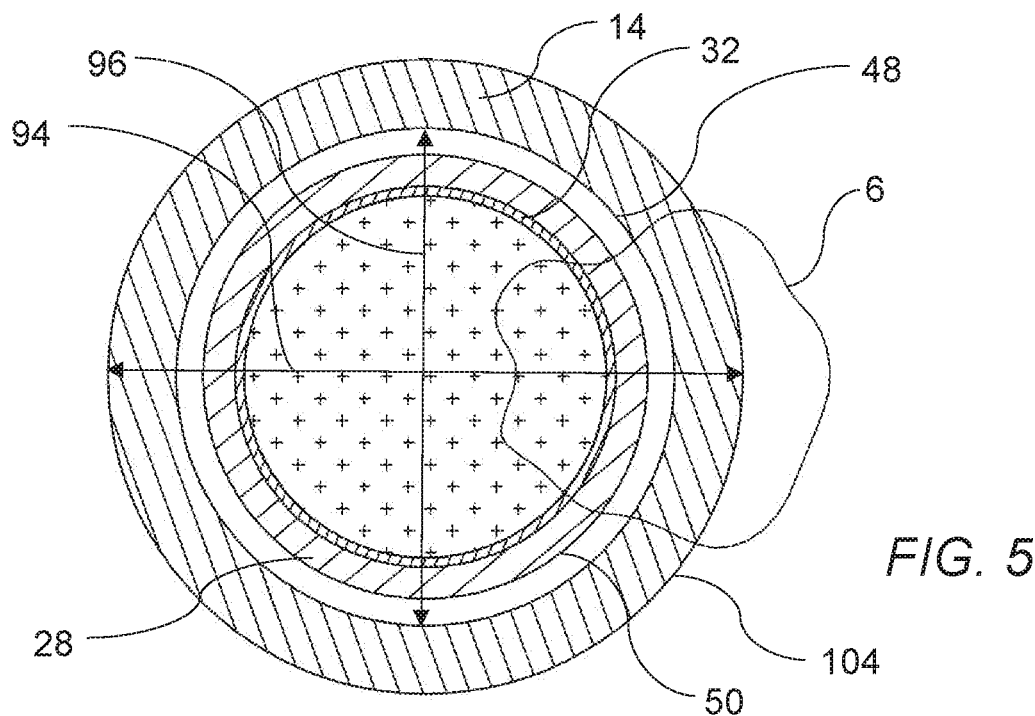
FIG. 5 is a transverse cross section view of the laser ablation of FIG. 2 taken across lines 5-5 of FIG. 2.

Between the proximal bond section and the distal bond section the outer jacket 230 may be unbonded to the catheter tube (see FIG. 5 wherein outer jacket embodiment 14 is similarly unbonded to the catheter tube 28). The outer jacket may include a tubular jacket body 256 that has a longitudinal stiffness which is greater than a longitudinal stiffness of the catheter tube 28 at the proximal portion 54 of the catheter tube 28. The tubular jacket body 256 may be configured in dimensions, materials, and features to increase the longitudinal stiffness and crush resistance of the respective laser ablation catheter 12 along a length of the outer jacket 230.

Figure 24:
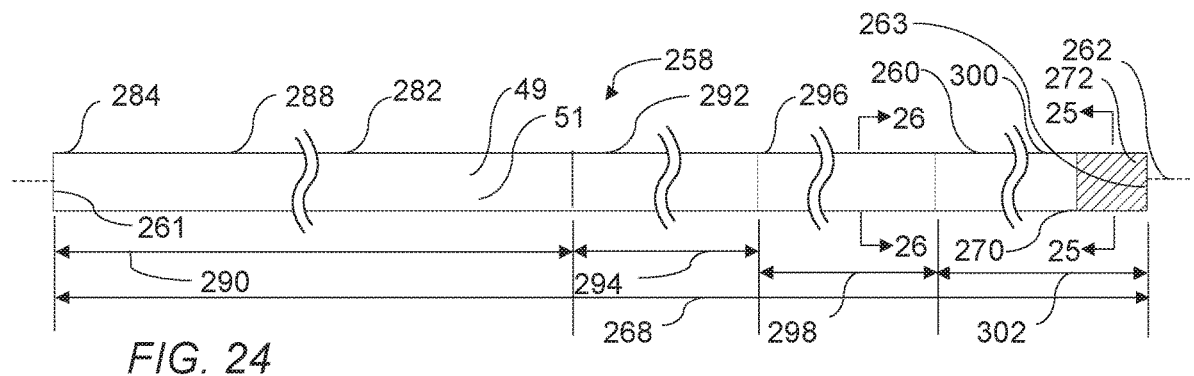
FIG. 24 is an elevation view of an outer jacket embodiment having a substantially constant transverse outer dimension and including a tubular reinforcement and a plurality of axial sections.
Figure 25:
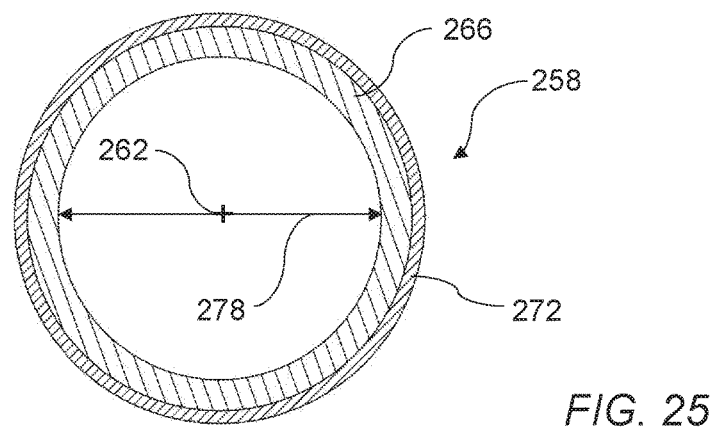
FIG. 25 is a transverse cross section view of the outer jacket embodiment of FIG. 24 taken along lines 25-25 of FIG. 24.
Figure 26:
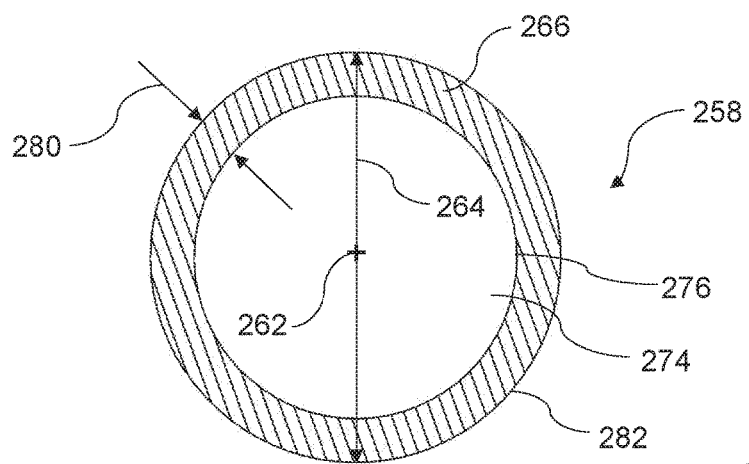
FIG. 26 is a transverse cross section view of the outer jacket embodiment of FIG. 24 taken along lines 26-26 of FIG. 24.

FIGS. 24-26 depict an embodiment of an outer jacket 258 which may include a plurality of sequential axial sections 260 which may be longitudinally disposed along a longitudinal axis 262 of the outer jacket 258, with each axial section 260 comprising a material having a flexural modulus which is different than the flexural moduli of respective adjacent axial section 262 materials. In some cases, the flexural modulus of each material of each respective sequential axial section 258 may decrease distally along the outer jacket 258. Each axial section 260 may be formed from any suitable polymer material such as Nylon®, Pebax®, or the like.

The outer jacket 258 may have a proximal end 261 that may be disposed at a proximal portion 54 of the catheter tube 28 of a respective laser ablation catheter embodiment and a distal end 263 that may be disposed at an axial position 58 that is about 10 cm to about 60 cm proximal of the distal end 44 of the catheter tube 28 (see FIG. 2). The outer jacket 258 may be secured relative to the catheter tube 28 such that the outer jacket 258 remains substantially fixed along a longitudinal axis 60 thereof relative to the catheter tube 28.

The outer jacket embodiment 258 which is depicted in FIG. 24 may have a substantially constant transverse outer dimension 264, may include a jacket body 266, and may have an axial length 268 (as shown in FIG. 24) of about 140 cm to about 180 cm. A distal portion 270 of the outer jacket 258 may include a radiopaque marker 272, the radiopaque marker 272 having any suitable any suitable feature, dimension, or material of any of the radiopaque marker embodiments discussed herein. The outer jacket 258 may include an inner lumen 274 having an inner surface 276 which may be configured to slide over the outer surface 50 of the catheter tube 28 with a close fit between the inner surface 276 and the outer surface 50. In some cases the close fit between the outer surface 276 of the catheter tube 28 and the inner surface 276 of the inner lumen 274 of the outer jacket 258 includes dimensional a clearance (see FIG. 6) of about 0.0005 inches to about 0.004 inches.

As discussed above, some embodiments of the catheter tube 28 may have an inner diameter 90 of about 0.043 inches, an outer diameter 92 of about 0.061 inches, and a corresponding wall thickness 100 of about 0.009 inches. The outer jacket embodiment 258 may have an inner diameter 278 of about 0.062 inches, an outer dimension 232 of about 0.070 inches, and a corresponding wall thickness 280 of about 0.004 inches. Hence a ratio of the outer jacket 258 wall thickness 280 to the wall thickness 100 of the catheter tube may be about 0.44 in some instances. In some cases, the ratio of the wall thickness 280 of the outer jacket 258 to the wall thickness 100 of the catheter tube 28 may be about 0.5 to about 0.9.

An outer surface 282 of the outer jacket 258 may be configured to easily slide into the inner lumen 106 of the support catheter 24, with the inner lumen 106 of the support catheter 24 having an inner surface 108 with diameter 110 that is at most one French larger than the outer dimension (diameter) 264 of the outer surface 50 of the catheter tube 28. Despite having a thinner wall thickness 280 relative to a wall thickness 100 of the catheter tube 28, the outer jacket 258 may still be configured such that it provides axial stiffness and crush resistance to the respective laser ablation catheter embodiment 12.

The outer jacket embodiment 258 may be secured relative to the catheter tube 28 such that the outer jacket 258 remains substantially fixed along a longitudinal axis 60 of the catheter tube 28. A proximal portion 284 of the outer jacket 258 may be adhesively bonded to the catheter tube 28 (see FIG. 8 for reference) by applying an adhesive 76 between the inner surface 276 of the outer jacket 258 and the outer surface 50 of the catheter tube 28 thereby forming a proximal bond section (which may be the same as or similar to proximal bond section 78 which is depicted in FIG. 10). In addition, a distal portion 270 of the outer jacket 258 may be adhesively bonded to the catheter tube 28 by applying an adhesive 76 between the inner surface 276 of the outer jacket 258 and the outer surface 50 of the catheter tube 28 thereby forming a distal bond section (which may be the same as or similar to distal bond section 79 which is depicted in FIG. 4). Any suitable adhesive 76 such as a cyanoacrylate, epoxy or the like may be used to create the proximal bond section and the distal bond section. For some embodiments, an axial length of the proximal bond section may be about 0.039 inches to about 0.787 inches and an axial length of the distal bond section may be about 0.039 inches to about 0.787 inches. Between the proximal bond section and the distal bond section the outer jacket 258 may be unbonded to the catheter tube 28 (see FIG. 5 wherein outer jacket embodiment 14 is similarly unbonded to the catheter tube 28).

Each axial section 260 of the outer jacket 258 may have a tubular configuration and each axial section 260 may be configured with the substantially constant transverse outer dimension 264. For some embodiments, each axial section 260 may be secured to a respective adjacent axial section 260 such as by thermal fusion thereby securing each axial section 260 to the respective adjacent axial section 260. Some axial sections 260 which may be disposed in the proximal portion 284 of the outer jacket 258 may be configured to increases the longitudinal stiffness and crush resistance of the respective laser ablation catheter 12 along a length of the outer jacket 258.

As an example, a first material of a respective first axial section 288 of the outer jacket embodiment 258 may include a material such as Nylon® 12, the first axial section 288 having an axial length 290 of about 150 cm to about 170 cm. A second material of a second axial section 292 of the outer jacket embodiment 258 may include a material such as Pebax® 7233, the second axial section 292 having an axial length 294 of about 0.5 cm to about 2 cm. Pebax® 7233 may have a flexural modulus of about 0.45 GPa to about 0.55 GPa in some cases. A third material of a third axial section 296 of the outer jacket embodiment 258 may include a material such as Pebax® 5533, the third axial section 296 having an axial length 298 of about 0.5 cm to about 2 cm. In some cases, Pebax® 5533 may have a flexural modulus of about 0.15 GPa to about 0.19 GPa. A fourth material of a fourth axial section 300 of the outer jacket embodiment 258 may include a material such as Pebax® 3533, the fourth axial section 300 having an axial length 302 of about 0.25 cm to about 1 cm.

As such, the first axial section 288 is the proximal most axial section and includes the material having the highest flexural modulus of the four axial sections 288, 292, 296, and 300. A distal end of the first axial section 288 is secured to a proximal end of the second axial section 292. The second axial section 292 is disposed axially between the first axial section 288 and the third axial section 296. The second axial section 292 includes a material having a flexural modulus which is lower than a flexural modulus of the material of the first axial section 288 and higher than a flexural modulus of a material of the third axial section 296. A distal end of the second axial section 292 is secured to a proximal end of the third axial section 296. A distal end of the third axial section 296 is secured to a proximal end of the fourth axial section 300. In addition, the flexural modulus of the material of the third axial section 296 is less than a flexural modulus of the material of the fourth axial section 300. For this embodiment, the flexural modulus of the materials of the respective axial sections 288, 292, 296, and 300 decreases distally along the outer jacket embodiment 258.

Another way of increasing the longitudinal stiffness and crush resistance of a proximal portion of an outer jacket embodiment while maintaining a flexible distal portion may be to vary the transverse outer dimension (outer diameter) of the respective jacket body along its axial length. For some such embodiments, the inner diameter of the outer jacket may remain substantially constant along the axial length of the outer jacket embodiment as the outer diameter varies. For some other embodiments, the inner diameter of the outer jacket may vary along the axial length of the outer jacket embodiment. Thus, the wall thickness of the outer jacket embodiment can be made thinner in a distal axial section of the outer jacket, and thicker in a proximal axial section of the outer jacket (with a tapered axial section disposed between the distal and proximal axial sections). For some outer jacket embodiments, the manipulation section may be disposed within a respective proximal axial section, which would have a greater wall thickness than a respective distal axial section. The manipulation section would thus provide greater kink/crush resistance than the more distal sections of the outer jacket embodiment due to the greater wall thickness.

Figure 27:
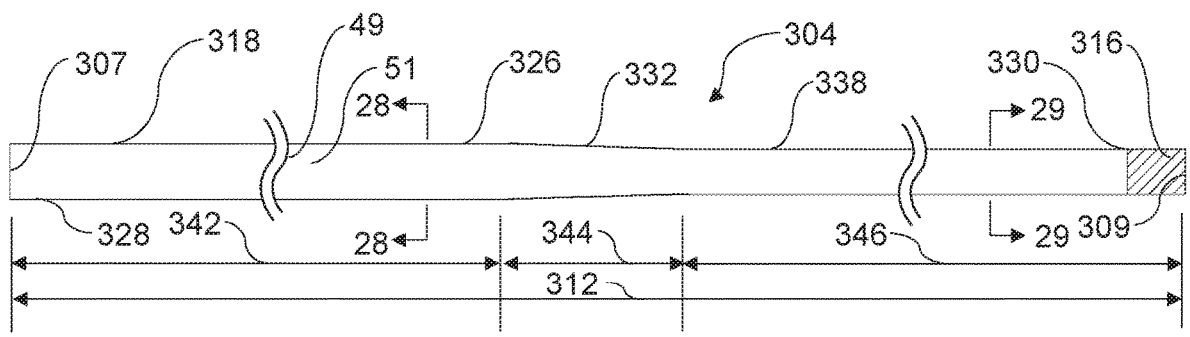
FIG. 27 is an elevation view of an outer jacket embodiment having multiple transverse outer dimensions.
Figure 28:
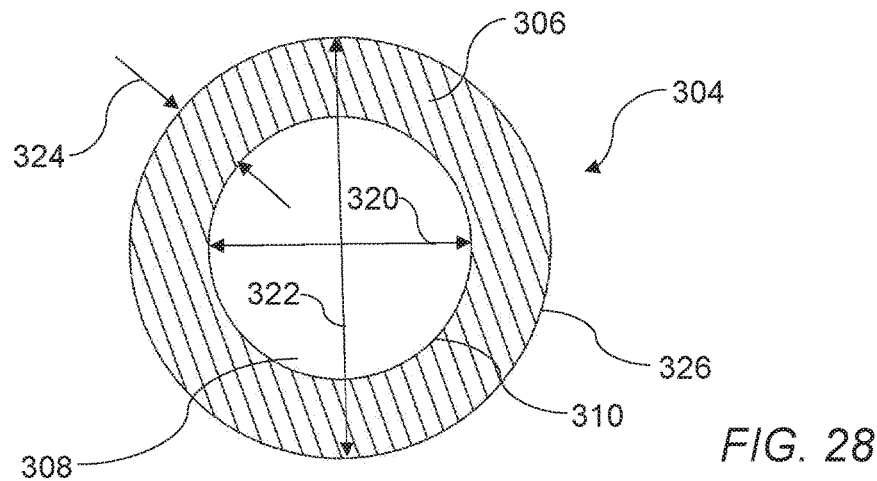
FIG. 28 is a transverse cross section view of the outer jacket embodiment of FIG. 27 taken along lines 28-28 of FIG. 27.
Figure 29:
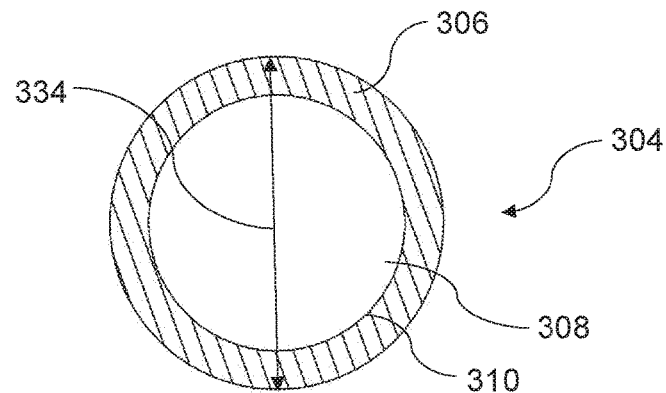
FIG. 29 is a transverse cross section view of the outer jacket embodiment of FIG. 27 taken along lines 29-29 of FIG. 27.

FIGS. 27-29 depict an embodiment of an outer jacket 304 which includes a tapered jacket body 306. In some cases a respective laser ablation catheter embodiment (such as the laser ablation catheter 12) may be configured to include the outer jacket embodiment 304 (which would replace outer jacket embodiment 14). The outer jacket 304 may have a proximal end 307 that may be disposed at a proximal portion 54 of the catheter tube 28 of a respective laser ablation catheter embodiment and a distal end 309 that may be disposed at an axial position 58 that is about 10 cm to about 60 cm proximal of the distal end 44 of the catheter tube 28 (see FIG. 2). The outer jacket 304 may be secured relative to the catheter tube 28 such that the outer jacket 304 remains substantially fixed along a longitudinal axis 60 thereof relative to the catheter tube 28.

The outer jacket embodiment 304 may have an inner lumen 308 with an inner surface 310, with the inner surface 310 of the inner lumen 308 being configured to slide over an exterior surface 50 of the catheter tube 28 with a close fit therebetween. In some cases the close fit between the outer surface 50 of the catheter tube 28 and the inner surface 310 of the inner lumen 308 of the outer jacket 304 includes a dimensional clearance (see FIG. 6) of about 0.0005 inches to about 0.004 inches.

Embodiments of the outer jacket 304 may have an axial length 312 (as shown in FIG. 27) of about 140 cm to about 180 cm. A distal portion 330 of the outer jacket 304 may include a radiopaque marker 316, the radiopaque marker 316 having any suitable any suitable feature, dimension, or material of any of the radiopaque marker embodiments discussed herein. As discussed above embodiments of the catheter tube 28 may have an inner diameter 90 of about 0.043 inches, an outer diameter 92 of about 0.061 inches, and a corresponding wall thickness 100 of about 0.009 inches. A proximal axial section 318 of the outer jacket 304 embodiment may have an inner diameter 320 of about 0.062 inches, an outer diameter 322 of about 0.070 inches, and a corresponding wall thickness 324 of about 0.004 inches. Hence along the proximal axial section 318 of the outer jacket 304, a ratio of the outer jacket 304 wall thickness 324 to the wall thickness 100 of the catheter tube 28 may be about 0.44. In some cases, the ratio of the wall thickness 324 of the outer jacket 304 to the wall thickness 100 of the catheter tube 28 may be about 0.5 to about 0.9 along the proximal axial section 318.

An outer surface 326 of the outer jacket 304 which is disposed along the proximal axial section 318 of the outer jacket 318 may be configured to easily slide into an inner lumen 106 of the support catheter 24 in some cases. The inner lumen 106 of the support catheter 24 having the inner surface 108 with diameter 110 that is in some cases at most one French larger than the diameter 92 of the outer surface 50 of the catheter tube 28. Despite having a thinner wall thickness 324 relative to a wall thickness 100 of the catheter tube 28, the outer jacket 304 may still be configured such that it provides axial stiffness and crush resistance to the respective laser ablation catheter embodiment 12 along the proximal axial section 318 of the outer jacket 304.

The outer jacket embodiment 304 may be secured relative to the catheter tube 28 such that the outer jacket 304 remains substantially fixed along a longitudinal axis 60 the catheter tube 28. A proximal portion 328 of the outer jacket 304 may be adhesively bonded to the catheter tube 28 (see FIG. 8 for reference) by applying an adhesive 76 between the inner surface 310 of the outer jacket 314 and the outer surface 50 of the catheter tube 28 thereby forming a proximal bond section (which may be the same as or similar to the proximal bond section 78 which is depicted in FIG. 10). In addition, a distal portion 330 of the outer jacket 304 may be adhesively bonded to the catheter tube 28 by applying an adhesive 76 between the inner surface 310 of the outer jacket 304 and the outer surface 50 of the catheter tube 28 thereby forming a distal bond section (which may be the same as or similar to distal bond section 79 which is depicted in FIG. 4). Any suitable adhesive 76 such as a cyanoacrylate, epoxy or the like may be used to create the proximal bond section and the distal bond section. For some embodiments, an axial length of the proximal bond section may be about 0.039 inches to about 0.787 inches and an axial length of the distal bond section may be about 0.039 inches to about 0.787 inches. Between the proximal bond section and the distal bond section the outer jacket 304 may be unbonded to the catheter tube 28 (see FIG. 5 wherein outer jacket embodiment 14 is similarly unbonded to the catheter tube 28).

Some portions of the jacket body 306 (such as the proximal axial section 318) may have a longitudinal stiffness which is greater than a longitudinal stiffness of the catheter tube 28 at the proximal portion 54 of the catheter tube 28. The jacket body 306 may have a tubular configuration and may include a tapered axial section 332 that tapers distally to a smaller outer transverse dimension 334 and cross section area with the jacket body 306 being configured to increase the longitudinal stiffness and crush resistance of the laser ablation catheter 12 over the proximal portion 54 of the catheter tube 28. The tapered axial section 332 may be disposed between a proximal axial section 318 which may have a transverse outer dimension 322 of about 0.016 inches to about 0.100 inches larger than the outer diameter 92 of the catheter tube 28, and a distal axial section 338 which may have a transverse outer dimension 334 of about 0.006 inches to about 0.10 inches larger than the outer diameter 92 of the catheter tube 28. In some cases, an axial length 342 of the proximal axial section 318 may be about 5 cm to about 20 cm, an axial length 344 of the tapered axial section 332 may be about 5 cm to about 15 cm, and an axial length 346 of the distal axial section 338 may be about 50 cm to about 150 cm. For some embodiments, the outer jacket 322 may be monolithically formed from a single material such as any suitable polymer including Nylon®, Pebax® or the like.

Figure 30:
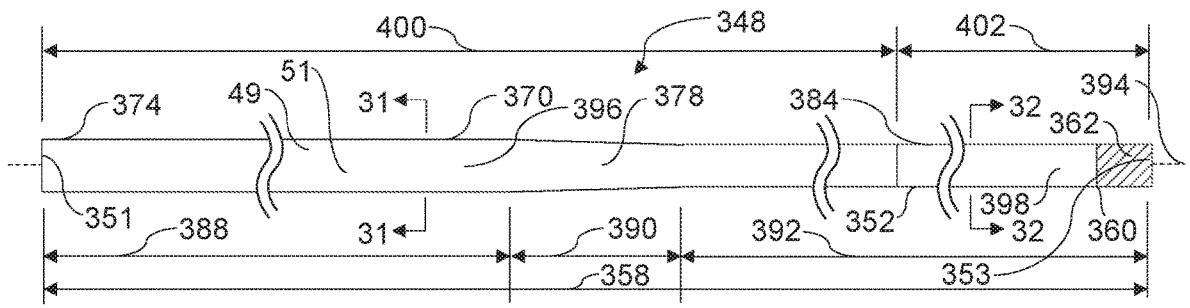
FIG. 30 is an elevation view of an outer jacket embodiment having multiple transverse outer dimensions and incorporating a plurality of axial sections.
Figure 31:
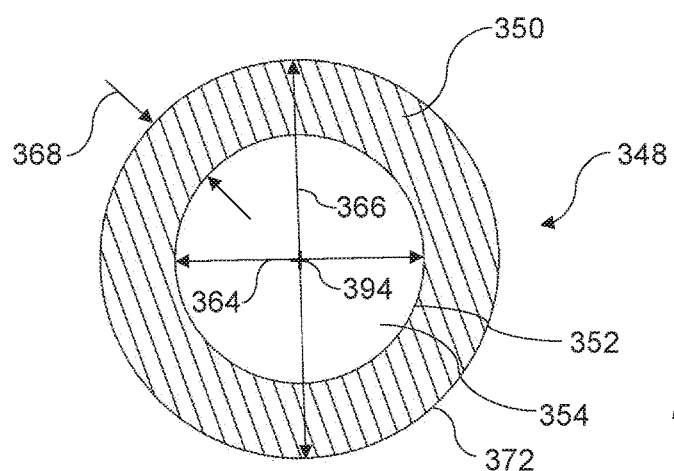
FIG. 31 is a transverse cross section view of the outer jacket embodiment of FIG. 30 taken along lines 31-31 of FIG. 30.
Figure 32:
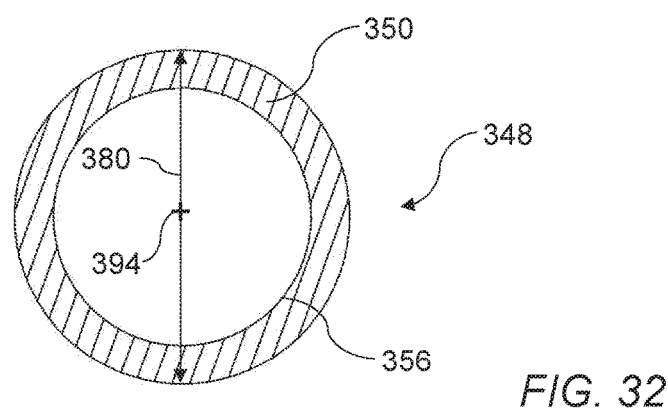
FIG. 32 is a transverse cross section view of the outer jacket embodiment of FIG. 30 taken along lines 32-32 of FIG. 30.

An embodiment of an outer jacket 348 having a dimensionally tapered jacket body 350 and a plurality of axial sections 352 defined by varying material properties is depicted in FIGS. 30-32. In some cases, a respective laser ablation catheter embodiment (such as the laser ablation catheter 12) may be configured to include the outer jacket embodiment 348 (which would replace outer jacket embodiment 14). The outer jacket 348 may have a proximal end 351 that may be disposed at a proximal portion 54 of the catheter tube 28 of a respective laser ablation catheter embodiment and a distal end 353 that is disposed at an axial position 58 that is about 10 cm to about 60 cm proximal of the distal end 44 of the catheter tube 28 (see FIG. 2). The outer jacket 348 may be secured relative to the catheter tube 28 such that the outer jacket 348 remains substantially fixed along a longitudinal axis 60 thereof relative to the catheter tube 28.

The outer jacket embodiment 348 may have an inner lumen 354 with an inner surface 356, with the inner surface 356 of the inner lumen 354 being configured to slide over an exterior surface 50 of the catheter tube 28 with a close fit therebetween. In some instances, the close fit between the outer surface 50 of the catheter tube 28 and the inner surface 356 of the inner lumen 354 of the outer jacket 348 includes a dimensional clearance (see FIG. 6) of about 0.0005 inches to about 0.004 inches.

Embodiments of the outer jacket 348 may have an axial length 358 (as shown in FIG. 30) of about 140 cm to about 180 cm. A distal portion 360 of the outer jacket 348 may include a radiopaque marker 362, the radiopaque marker 362 having any suitable any suitable feature, dimension, or material of any of the radiopaque marker embodiments discussed herein. As discussed above, embodiments of the catheter tube 28 may have an inner diameter 90 of about 0.043 inches, an outer diameter 92 of about 0.061 inches, and a corresponding wall thickness 100 of about 0.009 inches. In some instances, a proximal axial section 370 of the outer jacket embodiment 348 may have an inner diameter 364 of about 0.062 inches, an outer diameter 366 of about 0.070 inches, and a corresponding wall thickness 368 of about 0.004 inches. Hence a ratio of the outer jacket 348 wall thickness 368 to the wall thickness 100 of the catheter tube 28 may be about 0.44 along the proximal axial section 370. In some cases, the ratio of the wall thickness 368 of the outer jacket 348 to the wall thickness 100 of the catheter tube 28 may be about 0.5 to about 0.9 along the proximal axial section 370.

An outer surface 372 of the outer jacket 348 which is disposed along the proximal axial section 370 may be configured to easily slide into an inner lumen 106 of the support catheter 24 in some cases. The inner lumen 106 of the support catheter 24 having an inner surface 108 with diameter 110 that may be in some cases at most one French larger than a diameter 92 of the outer surface 50 of the catheter tube 28. Despite having a thinner wall thickness 368 relative to a wall thickness 100 of the catheter tube 28, the outer jacket 348 may still be configured such that it provides axial stiffness and crush resistance to the respective laser ablation catheter embodiment 12 along the proximal axial section 370 of the outer jacket 348.

The outer jacket embodiment 348 may be secured relative to the catheter tube 28 such that the outer jacket 348 remains substantially fixed along a longitudinal axis 60 of the catheter tube 28. A proximal portion 374 of the outer jacket 348 may be adhesively bonded to the catheter tube 28 (see FIG. 8 for reference) by applying an adhesive 76 between the inner surface 356 of the outer jacket 348 and the outer surface 50 of the catheter tube 28 thereby forming a proximal bond section (which may be the same as or similar to proximal bond section 78 which is depicted in FIG. 10). In addition, a distal portion 360 of the outer jacket 348 may be adhesively bonded to the catheter tube 28 by applying an adhesive 76 between the inner surface 356 of the outer jacket 348 and the outer surface 50 of the catheter tube 28 thereby forming a distal bond section (which may be the same as or similar to distal bond section 79 which is depicted in FIG. 4). Any suitable adhesive 76 such as a cyanoacrylate, epoxy or the like may be used to create the proximal bond section and the distal bond section. For some embodiments, an axial length of the proximal bond section may be about 0.039 inches to about 0.787 inches and an axial length of the distal bond section may be about 0.039 inches to about 0.787 inches. Between the proximal bond section and the distal bond section the outer jacket 348 may be unbonded to the catheter tube 28 (see FIG. 5 wherein outer jacket embodiment 14 is similarly unbonded to the catheter tube 28).

Some portions of the jacket body 350 (such as the proximal axial section 370) may have a longitudinal stiffness which is greater than a longitudinal stiffness of the catheter tube 28 at the proximal portion 54 of the catheter tube 28. The jacket body 350 may have a tubular configuration and may include a tapered axial section 378 that tapers distally to a smaller outer transverse dimension 380 and cross section area with the tubular jacket body 350 being configured to increase the longitudinal stiffness and crush resistance of the laser ablation catheter 12 over the proximal portion 54 of the catheter tube 28.

The tapered axial section 378 may be disposed between the proximal axial section 370 which may have a transverse outer dimension 366 of about 0.016 inches to about 0.100 inches larger than the outer diameter 92 of the catheter tube 28, and a distal axial section 384 having a transverse outer dimension 380 of about 0.006 inches to about 0.010 inches larger than the outer diameter 92 of the catheter tube 28. In some instances, an axial length 388 of the proximal axial section 370 may be about 5 cm to about 20 cm, an axial length 390 of the tapered axial section 378 may be from about 5 cm to about 15 cm, and an axial length 392 of the distal axial section 384 may be from about 50 cm to about 150 cm.

Some embodiments of the outer jacket 348 may include a plurality of material based sequential axial sections 352 which are longitudinally disposed along the longitudinal axis 394 of the outer jacket 348, with each axial section 352 formed from a material having a flexural modulus which is different than the flexural moduli of respective adjacent axial section 352 materials. In some cases, the flexural modulus of each material of each respective sequential axial section 352 may decrease distally along the outer jacket 348. For example, a first material of a respective first axial section 396 may be formed from Nylon® 12 and a second material of a second axial section 398 may be formed from Pebax® 7233. In some instances, Pebax® 7233 may have a flexural modulus of about 0.45 GPa to about 0.55 GPa as discussed above.

In some cases, the first axial section 396 may have an axial length 400 of about 1 cm to about 5 cm, and the second axial section 398 may have an axial length 402 of about 0.2 cm to about 5 cm. For some embodiments, each axial section 352 may be secured to a respective adjacent axial section 352 such as by thermal fusion thereby securing each axial section 352 to the respective adjacent axial section 352. As such, the first axial section 396 is the proximal most axial section and includes the material having the highest flexural modulus of the two axial sections 396 and 398. A distal end of the first axial section 396 is secured to a proximal end of the second axial section 398.

Figure 33:
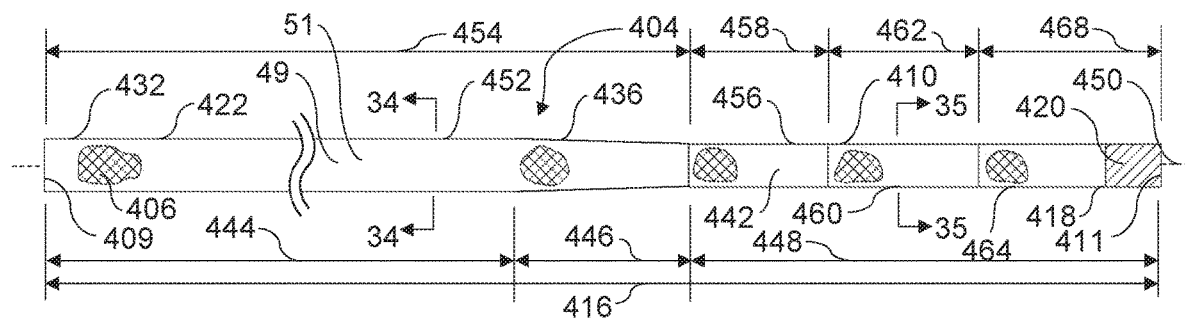
FIG. 33 is an elevation view of an outer jacket embodiment having multiple transverse outer dimensions, a tubular reinforcement, and a plurality of axial sections.
Figure 34:
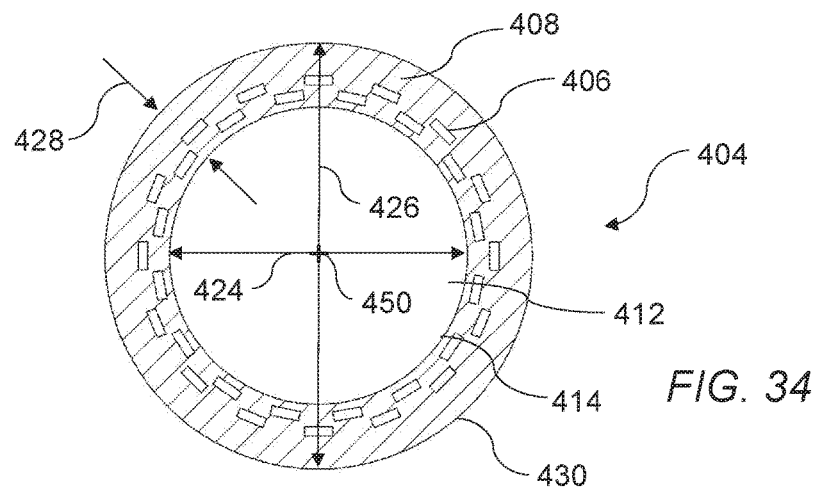
FIG. 34 is a transverse cross section view of the outer jacket embodiment of FIG. 33 taken along lines 34-34 of FIG. 33.
Figure 35:
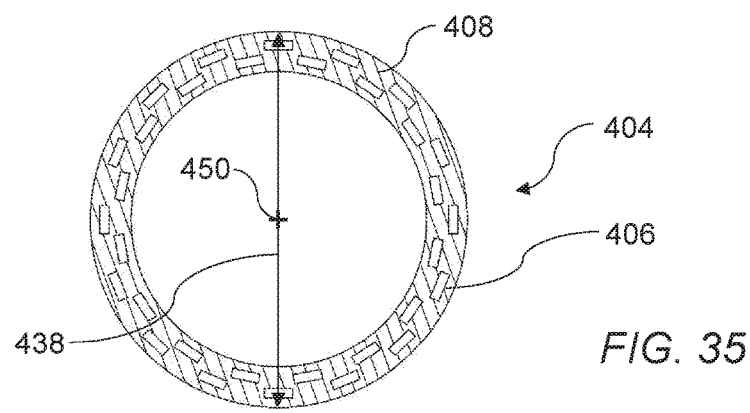
FIG. 35 is a transverse cross section view of the outer jacket embodiment of FIG. 33 taken along lines 35-35 of FIG. 33.

An embodiment of an outer jacket 404 which includes a tubular reinforcement 406, a tapered jacket body 408, and multiple material based axial sections 410 is depicted in FIGS. 33-35. In some cases a respective laser ablation catheter embodiment (such as the laser ablation catheter 12) may be configured to include the outer jacket embodiment 404 (which would replace outer jacket embodiment 14). The outer jacket 404 may have a proximal end 409 that may be disposed at a proximal portion 54 of the catheter tube 28 of a respective laser ablation catheter embodiment and a distal end 411 that may be disposed at an axial position 58 that is about 10 cm to about 60 cm proximal of the distal end 44 of the catheter tube 28 (see FIG. 2). The outer jacket 404 may be secured relative to the catheter tube 28 such that the outer jacket 404 remains substantially fixed along a longitudinal axis 60 thereof relative to the catheter tube 28.

The outer jacket 404 may include a tubular configuration having an inner lumen 412 with an inner surface 414, with the inner surface 414 of the inner lumen 412 being configured to slide over an exterior surface 50 of the catheter tube 28 with a close fit therebetween. In some instances, the close fit between the outer surface 50 of the catheter tube 28 and the inner surface 414 of the inner lumen 412 of the outer jacket 404 includes a dimensional clearance (see FIG. 6) of about 0.0005 inches to about 0.004 inches.

Embodiments of the outer jacket 404 may have an axial length 416 (as shown in FIG. 33) of about 140 cm to about 180 cm. A distal portion 418 of the outer jacket 404 may include a radiopaque marker 420, the radiopaque marker 420 having any suitable any suitable feature, dimension, or material of any of the radiopaque marker embodiments discussed herein. As discussed above, embodiments of the catheter tube 28 may have an inner diameter 90 of about 0.043 inches, an outer diameter 92 of about 0.061 inches, and a corresponding wall thickness 100 of about 0.009 inches. In some cases a proximal axial section 422 of the outer jacket embodiment 404 may have an inner diameter 424 of about 0.062 inches, an outer diameter 426 of about 0.070 inches, and a corresponding wall thickness 428 of about 0.004 inches. Hence a ratio of the outer jacket 404 wall thickness 428 to a wall thickness 100 of the catheter tube 28 may be about 0.44 along the proximal axial section 422. In some cases, the ratio of the wall thickness 428 of the outer jacket 404 to the wall thickness 100 of the catheter tube 28 may be about 0.5 to about 0.9 along the proximal axial section 422.

An outer surface 430 of the outer jacket 404 which is disposed along the proximal axial section 422 may be configured to easily slide into an inner lumen 106 of the support catheter 24 in some cases. The inner lumen 106 of the support catheter 24 having an inner surface 108 with diameter 110 that may be in some cases at most one French larger than a diameter 92 of the outer surface 50 of the catheter tube 28. Despite having a thinner wall thickness 428 relative to a wall thickness 100 of the catheter tube 28, the outer jacket 404 may still be configured such that it provides axial stiffness and crush resistance to the respective laser ablation catheter embodiment 12 along the proximal axial section 422 of the outer jacket 404.

The outer jacket embodiment 404 may be secured relative to the catheter tube 28 such that the outer jacket 404 remains substantially fixed along a longitudinal axis 60 of the catheter tube 28. A proximal portion 432 of the outer jacket 404 may be adhesively bonded to the catheter tube 28 (see FIG. 8 for reference) by applying an adhesive 76 between the inner surface 414 of the outer jacket 404 and the outer surface 50 of the catheter tube 28 thereby forming a proximal bond section (which may be the same as or similar to proximal bond section 78 which is depicted in FIG. 10). In addition, a distal portion 418 of the outer jacket 404 may be adhesively bonded to the catheter tube 28 by applying an adhesive 76 between the inner surface 414 of the outer jacket 404 and the outer surface 50 of the catheter tube 28 thereby forming a distal bond section (which may be the same as or similar to distal bond section 79 which is depicted in FIG. 4). Any suitable adhesive 76 such as a cyanoacrylate, epoxy or the like may be used to create the proximal bond section and the distal bond section. For some embodiments, an axial length of the proximal bond section may be about 0.039 inches to about 0.787 inches and an axial length of the distal bond section may be about 0.039 inches to about 0.787 inches. Between the proximal bond section and the distal bond section the outer jacket 404 may be unbonded to the catheter tube 28 (see FIG. 5 wherein outer jacket embodiment 14 is similarly unbonded to the catheter tube 28).

Some portions of the jacket body 408 (such as the proximal axial section 422) may have a longitudinal stiffness which is greater than a longitudinal stiffness of the catheter tube 28 at the proximal portion 54 of the catheter tube 28. The jacket body 408 may have an overall tubular configuration and may include a tapered axial section 436 that tapers distally to a smaller outer transverse dimension 438 and cross section area with the tubular jacket body 408 being configured to increase the longitudinal stiffness and crush resistance of the laser ablation catheter 12 over the proximal portion 54 of the catheter tube 28. The tapered axial section 436 may be disposed between a proximal axial section 422 which may have a transverse outer dimension 438 of about 0.016 inches to about 0.100 inches larger than the outer diameter 92 of the catheter tube 28, and a distal axial section 442 having the transverse outer dimension 436 of about 0.006 inches to about 0.010 inches larger than the outer diameter 92 of the catheter tube 28. In some instances, an axial length 444 of the proximal axial section 422 may be about 5 cm to about 20 cm, an axial length 446 of the tapered axial section 436 may be from about 5 cm to about 15 cm, and an axial length 448 of the distal axial section 442 may be from about 50 cm to about 150 cm.

The outer jacket 404 may also include a plurality of material based sequential axial sections 410 which may be longitudinally disposed along a longitudinal axis 450 of the outer jacket 404, with each axial section 410 formed from a material having a flexural modulus which is different than the flexural moduli of respective adjacent axial section materials 410. In some cases, the flexural modulus of each material of each respective sequential axial section 410 may decrease distally along the outer jacket embodiment 404.

As an example, a first material of a respective first axial section 452 of the outer jacket embodiment 404 may include a material such as Nylon® 12, the first axial section 452 having an axial length 454 of about 150 cm to about 170 cm. A second material of a second axial section 456 of the outer jacket embodiment 404 may include a material such as Pebax® 7233, the second axial section 456 having an axial length 458 of about 0.5 cm to about 2 cm. A third material of a third axial section 460 of the outer jacket embodiment 404 may include a material such as Pebax® 5533, the third axial section 460 having an axial length 462 of about 0.5 cm to about 2 cm. A fourth material of a fourth axial section 464 of the outer jacket embodiment 404 may include a material such as Pebax® 3533, the fourth axial section 464 having an axial length 468 of about 0.25 cm to about 1 cm.

As such, the first axial section 452 is the proximal most axial section and includes the material having the highest flexural modulus of the four axial sections 452, 456, 460, and 464. A distal end of the first axial section 452 is secured to a proximal end of the second axial section 456. The second axial section 456 is disposed axially between the first axial section 452 and the third axial section 460. The second axial section 456 includes a material having a flexural modulus which is lower than a flexural modulus of the material of the first axial section 452 and higher than a flexural modulus of a material of the third axial section 460. A distal end of the second axial section 456 is secured to a proximal end of the third axial section 460. A distal end of the third axial section 460 is secured to a proximal end of the fourth axial section 464. In addition, the flexural modulus of the material of the third axial section 460 is less than a flexural modulus of the material of the fourth axial section 464. For this embodiment, the flexural modulus of the materials of the respective axial sections 452, 456, 460, and 464 decreases distally along the outer jacket embodiment 404.

The longitudinal stiffness of the outer jacket 404 may be made greater than the longitudinal stiffness of the catheter tube 28 in some axial sections via the addition of the tubular reinforcement 406 and via variation of the flexural modulus of those axial sections 410. In some instances, each axial section 410 may be secured to a respective adjacent axial section 410 such as by thermal fusion thereby securing each axial section 410 to the respective adjacent axial section 410. Each axial section 410 of the outer jacket embodiment 404 may be configured as has been previously discussed wherein the tubular reinforcement embodiments 406 may be disposed within a wall of the jacket body 48 or disposed between layers of jacket body 408 materials. The tubular reinforcement 406 may thus disposed along each axial section 410 of the tubular jacket body 408, with the tubular jacket body 408 and tubular reinforcement 406 being configured to increase the longitudinal stiffness and crush resistance of the laser ablation catheter embodiment 12 along the proximal axial section 422. Any of the tubular reinforcement embodiments discussed herein may be utilized as the tubular reinforcement 406 for the outer jacket embodiment 404 depicted in FIGS. 33-35.

The optical fluid 34 of the laser ablation catheter 12 may typically be disposed within the inner lumen 30 of the catheter tube 28. It may also be important in some cases to maintain the inner lumen 30 of the catheter tube 28 in a completely filled state without voids or bubbles in the optical fluid 34 that might impair transmission of laser energy therethrough. Typically, the materials of the catheter tube 28 may include fluoropolymers such as FEP, EFEP, ETFE and the like. Many fluoropolymer materials are fluid permeable over extended periods of time. Upon storage of a liquid filled laser ablation catheter 12 utilizing a fluoropolymer catheter tube 28, the optical fluid 34 may diffuse through the catheter tube 28 and then vaporize on the outer surface 50 of the catheter tube 28 thus potentially leaving voids or bubbles in the optical fluid 34 within the inner lumen 30 of the catheter tube 28. A solution to this issue is to cover the catheter tube 28 with a fluid impermeable outer jacket 470 having an inner lumen 472 which completely encapsulates the outer surface 50 of the catheter tube 28 and thereby creates a vapor barrier. Hence optical fluid 34 diffusing through the wall of the catheter tube 28 will vaporize on the outer surface 50 of the catheter tube 28, and a vapor barrier will be formed between an inner surface 474 of the outer jacket 470 and the outer surface 50 of the catheter tube 50 which prevents further diffusion.

Figure 36:
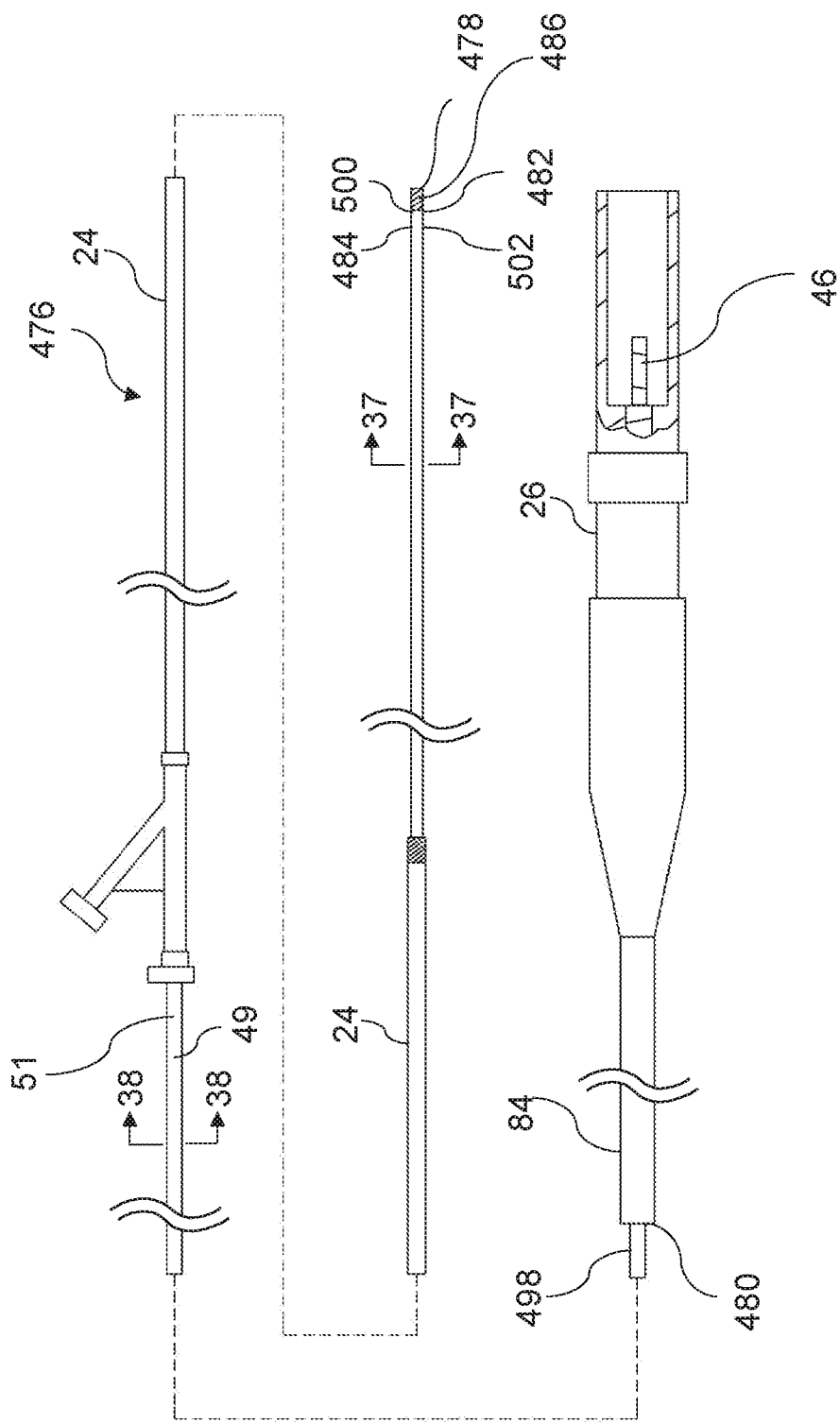
FIG. 36 is an elevation view in partial section of a laser ablation catheter embodiment including a water impermeable outer jacket and a guiding catheter.
Figure 37:
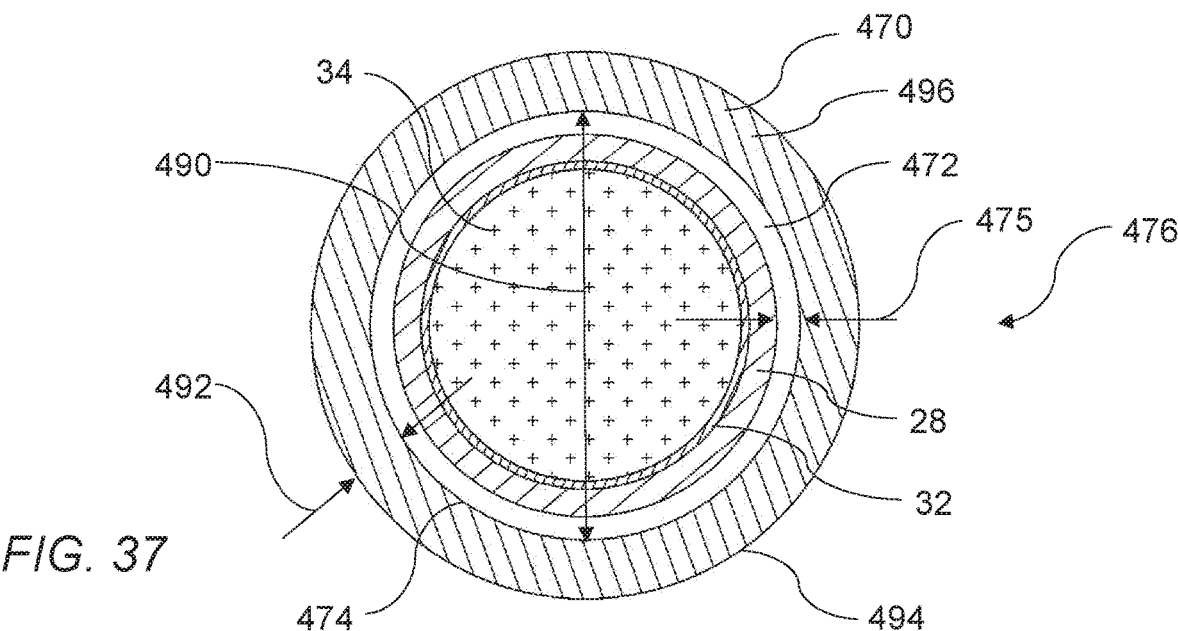
FIG. 37 is a transverse cross section view of the outer jacket embodiment of FIG. 36 taken along lines 37-37 of FIG. 36.
Figure 38:
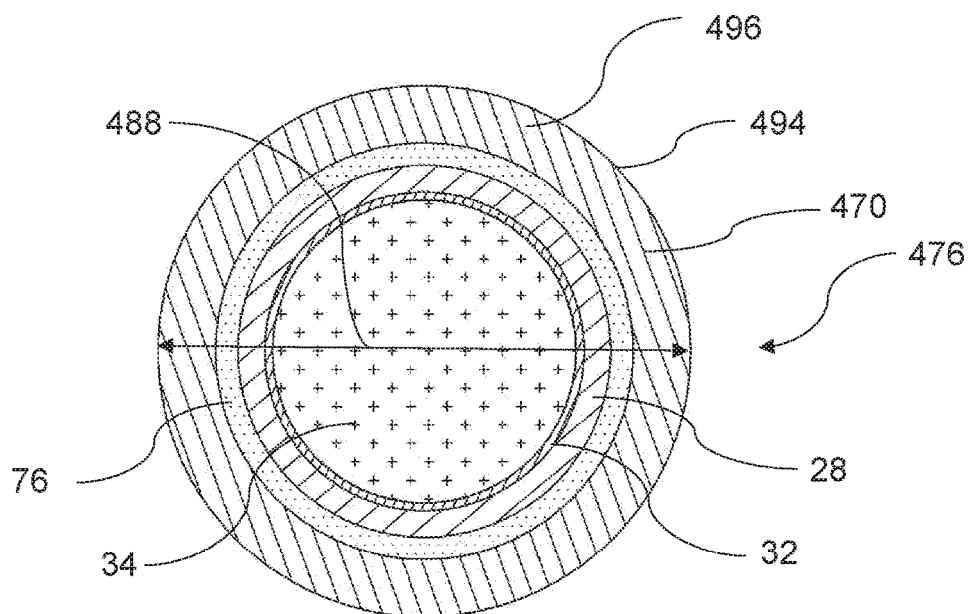
FIG. 38 is a transverse cross section view of the outer jacket embodiment of FIG. 36 taken along lines 38-38 of FIG. 36.

An embodiment of a laser ablation catheter 476 including the fluid impermeable outer jacket 470 is depicted in FIGS. 36-38. The laser ablation catheter 476 may have the same or similar dimensions, materials, features etc. as discussed previously with regard to laser ablation catheter embodiment 12. In particular, in some instances, laser ablation catheter embodiment 476 may include an outer jacket embodiment 470 in place of outer jacket embodiment 14 with respect to laser ablation catheter embodiment 12. The laser ablation catheter 476 may include a liquid filled waveguide which is configured for the propagation of high powered laser energy through the laser ablation catheter for the purposes of ablating blockages in the human body or any other suitable indication. The waveguide may include a tubular catheter tube 28 having an inner lumen 30 and an inner layer 32 which is disposed on an inner surface 33 of the inner lumen 30, the material of the inner layer 32 comprising an optical coating having a first index of refraction. The liquid filled waveguide may also include a biocompatible ultraviolet transparent optical fluid 34 which is disposed within and completely filling the inner lumen 30 of the catheter tube 28 without any significant bubbles or voids within the optical fluid 34. The optical fluid 34 may have a second index of refraction which is greater than the first index of refraction of the inner layer 32. The different indices of refraction of the materials at an optical boundary disposed between the inner layer 32 and the optical fluid 34 allow for total internal reflection and propagation of high powered laser energy through the waveguide.

The laser ablation catheter 476 may also include an ultraviolet grade elongated distal optical window 478 which may be disposed in liquid sealed relation to the inner surface 33 of the catheter tube 28 at the distal end 44 of the catheter tube 28. The distal optical window 478 may be in optical communication with the optical fluid 34 which is disposed within the inner lumen 30 of the catheter tube 38 thereby allowing for the transmission of laser energy from the optical fluid 24 through the distal optical window 478.

The laser ablation catheter 476 may also include an optical window 46 which is disposed within the laser coupler 24, with the optical window 46 being disposed in a liquid sealed relation to the inner surface 33 of the catheter tube 28. The optical window 46 is thus configured to be in direct optical communication and direct contact with the optical fluid 34 thereby allowing for the optical transmission of laser energy from the laser source 11, through the optical window, and into the optical fluid 34. The laser energy may then be propagated through the waveguide (formed by the catheter tube 28, the inner layer 32, and the optical fluid) through the distal optical window 478, emitted from an output surface of the distal optical window 478 and into a blockage disposed within a human body or any other suitable target.

The laser ablation catheter 476 may also include the outer jacket 470 that may be disposed over the catheter tube 28. A proximal end 480 of the outer jacket 470 may be disposed at a proximal portion 54 including a proximal end of the catheter tube 28 and a distal end 482 of the outer jacket 470 may be disposed at an axial position which is substantially adjacent to the distal end 44 of the catheter tube 28. The outer jacket 470 may be secured relative to the catheter tube 28 such that the outer jacket 470 remains substantially fixed along a longitudinal axis 60 of the catheter tube 28.

The outer jacket 470 may have an axial length of about 180 cm to about 220 cm which may be substantially equivalent to the axial length 70 of the respective catheter tube 28. A distal portion 484 of the outer jacket 470 may include a radiopaque marker 486, the radiopaque marker 486 having any suitable any suitable feature, dimension, or material of any of the radiopaque marker embodiments discussed herein. As discussed above, some embodiments of the catheter tube may have an inner diameter of about 0.043 inches, an outer diameter of about 0.061 inches, and a corresponding wall thickness of about 0.009 inches. The outer jacket embodiment 470 may have an inner diameter 490 of about 0.062 inches, an outer diameter 488 of about 0.070 inches, and a corresponding wall thickness 492 of about 0.004 inches. Hence a ratio of the outer jacket 470 wall thickness 492 to the wall thickness 100 of the catheter tube 28 may be about 0.44. In some cases, the ratio of the wall thickness 492 of the outer jacket 470 to the wall thickness 100 of the catheter tube 28 may be about 0.5 to about 0.9.

An outer surface 494 of the outer jacket 470 may be configured to easily slide into the inner lumen 106 of the support catheter 24, with the inner lumen 106 of the support catheter 24 in some cases having an inner surface 108 with diameter 110 that is at most one French larger than a diameter 92 of the outer surface 50 of the catheter tube 28. Despite having a thinner wall thickness 492 relative to the wall thickness 100 of the catheter tube 28, the outer jacket 470 may still be configured such that it provides axial stiffness and crush resistance to the laser ablation catheter embodiment 476.

In some cases, the outer jacket 470 may be configured with a substantially constant transverse outer diameter 488 and may include the inner lumen 472 having the inner surface 474. The inner surface 474 of the inner lumen 472 of the outer jacket 470 may be configured to slide over the outer surface 50 of the catheter tube 28 with a close fit therebetween. In some instances, the close fit between the outer surface 50 of the catheter tube 28 and the inner surface 474 of the inner lumen 472 of the outer jacket 470 includes a dimensional clearance 475 (see FIG. 37) of about 0.0005 inches to about 0.004 inches. The outer jacket 470 may include a tubular jacket body 496 which may have a longitudinal stiffness greater than a longitudinal stiffness of the catheter tube 28 at the proximal portion of the catheter tube 54.

The tubular jacket body 496 may be formed from a jacket body 496 material that is water impermeable, and the tubular jacket body 496 may be configured in dimension, material(s), etc. to increase the longitudinal stiffness and crush resistance of the laser ablation catheter 476. In some cases the outer jacket 470 may be monolithically formed from a single continuous piece of material such as PCTFE in order to provide an outer vapor barrier for the optical fluid disposed within the catheter tube 28. For some embodiments (not shown) the tubular jacket body 496 may taper from the proximal end 480 of the tubular jacket body 496 to a smaller outer transverse dimension and cross section area at the distal end 482 of the tubular jacket body 496.

The outer jacket embodiment 470 may be secured relative to the catheter tube 28 such that the outer jacket 470 remains substantially fixed along the longitudinal axis 60 of the catheter tube 28. A proximal portion 498 of the outer jacket 470 may be adhesively bonded to the catheter tube 28 (see FIG. 8 for reference) by applying an adhesive 76 between the inner surface 474 of the outer jacket 470 and the outer surface 50 of the catheter tube 28 thereby forming a proximal bond section (which may be the same as or similar to proximal bond section 78 which is depicted in FIG. 10). In addition, a distal portion 500 of the outer jacket 470 may be adhesively bonded to the catheter tube 28 by applying an adhesive 76 between the inner surface 474 of the outer jacket 470 and the outer surface 50 of the catheter tube 28 thereby forming a distal bond section (which may be the same as or similar to distal bond section 79 which is depicted in FIG. 4). Any suitable adhesive 76 such as a cyanoacrylate, epoxy or the like may be used to create the proximal bond section and the distal bond section. For some embodiments, an axial length of the proximal bond section may be about 0.039 inches to about 0.787 inches and an axial length of the distal bond section may be about 0.039 inches to about 0.787 inches. Between the proximal bond section and the distal bond section the outer jacket 470 may be unbonded to the catheter tube 28 (see FIG. 5 wherein outer jacket embodiment 14 is similarly unbonded to the catheter tube 28).

As discussed above, laser ablation catheters embodiments which are configured with an outer jacket can be manufactured such that the waveguide and associated materials (catheter tube and the inner layer) may be thermally cycled separately from the other components of the laser ablation catheter embodiments. Thus, the laser ablation catheter 12 which is configured with an outer jacket 14 may be made as follows. The inside surface 33 of the catheter tube 28 may be coated with an optical coating having a first index of refraction. An appropriate thermal cycle may then be applied to the catheter tube 28 and the optical coating to adhere the optical coating to the inner surface 33 of the catheter tube 28 thereby forming the inner layer 32.

An elongated distal optical window 40 may then be attached to a distal portion 502 of the catheter tube 28. The catheter tube 28 may then be filled with a biocompatible ultraviolet transparent optical fluid 34 having a second index of refraction. A high energy laser coupler 26 may then be attached to a proximal portion 54 of the catheter tube 28 with the laser coupler 26 having a laser coupler body, a window connector body being disposed within the optical coupler body, and an optical input window disposed within and secured to the window connector body with the optical window being in optical communication with the optical fluid 34.

Laser light may then be transmitted through the optical fluid 34 in order to determine the optical performance of the optical coating/inner layer 32. The outer jacket 14 may then be slid over the catheter tube 28. In some instances, the distal end 56 of the outer jacket 14 may be slid over the catheter tube to a distance of about 10 cm to about 60 cm proximal of the distal end 44 of the catheter tube 28. In some cases, the distal end 56 of the outer jacket 14 may be slid to the distal end 44 of the catheter tube 28.

The outer jacket 14 may include the inner lumen 88 having an inner surface 48 which is configured to slide over an outer surface 50 of the catheter tube 28 with a close fit therebetween. In some cases the close fit between the outer surface 50 of the catheter tube 28 and the inner surface 48 of the inner lumen 88 of the outer jacket 14 includes a dimensional clearance 98 (see FIG. 6) of about 0.0005 inches to about 0.004 inches.

The outer jacket 14 or any other suitable outer jacket embodiment discussed herein may then be secured to the catheter tube 28 such that the outer jacket 14 remains substantially fixed in relation to a longitudinal axis 60 the catheter tube 28, with the outer jacket 14 being configured to increase the longitudinal stiffness and crush resistance of the laser ablation catheter 12. The proximal portion 74 of the outer jacket 14 may be adhesively bonded to the catheter tube 28 thereby forming a proximal bond section 78 utilizing any suitable adhesive 76 such as cyanoacrylate or the like. The distal portion 64 of the outer jacket 14 may be adhesively bonded to the catheter tube 28 thereby forming a distal bond section 79 utilizing any suitable adhesive 76 such as cyanoacrylate or the like. For some embodiments the axial length 81 of the proximal bond section 78 may be about 0.039 inches to about 0.787 inches (see FIG. 10 for reference), and the axial length 80 of the distal bond section 79 may be about 0.039 inches to about 0.787 inches (see FIG. 4 for reference).

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. A laser ablation catheter, comprising:
    a liquid filled waveguide including a catheter tube having an inner layer with a first index of refraction and an optical fluid disposed within and completely filling an inner lumen of the catheter tube, the optical fluid having a second index of refraction which is greater than the first index of refraction;
    a distal optical window disposed in liquid sealed relation to an inner surface of the catheter tube at a distal end of the catheter tube and in optical communication with the optical fluid;
    an optical input window disposed in a liquid sealed relation to the inner surface of the catheter tube at a proximal end of the catheter tube and in optical communication with the optical fluid; and
    an outer jacket that is disposed over the surface of the catheter tube and that has a proximal end that is disposed at a proximal portion of the catheter tube and a distal end that is disposed at an axial position that is about 10 cm to about 60 cm proximal of a distal end of the catheter tube with the outer jacket being secured relative to the catheter tube such that the outer jacket remains substantially fixed along a longitudinal axis thereof relative to the catheter tube, the outer jacket comprising:
        a tubular configuration having an inner lumen with an inner surface, with the inner surface of the inner lumen being configured to slide over an exterior surface of the catheter tube with a close fit therebetween;
        a tubular jacket body that has a longitudinal stiffness greater than a longitudinal stiffness of the catheter tube at the proximal portion of the catheter tube, and
        a tubular reinforcement that is crush resistant and disposed along the tubular jacket body with the tubular jacket body and reinforcement being configured to increase the stiffness and crush resistance of the laser ablation catheter.

2. The laser ablation catheter of claim 1 wherein the close fit between the outer surface of the catheter tube and the inner surface of the inner lumen of the outer jacket comprises a clearance of about 0.0005 inches to about 0.004 inches.

3. The laser ablation catheter of claim 1 wherein a wall thickness of the outer jacket is thinner than a wall thickness of the catheter tube.

4. The laser ablation catheter of claim 3 wherein a ratio of the wall thickness of the outer jacket to the wall thickness of the catheter tube is from about 0.5 to about 0.9.

5. The laser ablation catheter of claim 1 wherein the jacket body comprises a tubular inner jacket layer having an inner lumen which is configured to slide over the catheter tube with the tubular reinforcement being disposed on an outer surface of the inner jacket layer, and a tubular outer jacket layer having an inner lumen with interior surface which covers the tubular reinforcement.

6. The laser ablation catheter of claim 1 further comprising a radiopaque marker which is disposed at a distal portion of the outer jacket, the radiopaque marker allowing for visualization of the distal end of the outer jacket through standard fluoroscopic imaging.

7. The laser ablation catheter of claim 6 wherein the radiopaque marker comprises an axial section of the jacket body which is infused with barium sulfate, the axial section disposed proximal and substantially adjacent to the distal end of the outer jacket.

8. The laser ablation catheter of claim 1 wherein the tubular reinforcement comprises a reinforcement wire having a substantially round transverse cross section and which is formed into a tubular coil.

9. The laser ablation catheter of claim 8 wherein the diameter of the reinforcement wire is from about 0.0005 inches to about 0.01 inches.

10. The laser ablation catheter of claim 8 wherein the reinforcement wire comprises a metal.

11. The laser ablation catheter of claim 8 wherein reinforcement wire comprises a para-aramid synthetic fiber.

12. The laser ablation catheter of claim 1 wherein the tubular reinforcement comprises a reinforcement ribbon having a substantially rectangular transverse cross section and which is formed into a tubular coil.

13. The laser ablation catheter of claim 12 wherein the reinforcement ribbon comprises a metal.

14. The laser ablation catheter of claim 12 wherein the reinforcement ribbon comprises a para-aramid synthetic fiber.

15. The laser ablation catheter of claim 1 wherein the tubular reinforcement comprises a plurality of reinforcement ribbons each having a substantially rectangular transverse cross section and each formed into a tubular braid.

16. The laser ablation catheter of claim 15 wherein each reinforcement ribbon comprises a metal.

17. The laser ablation catheter of claim 15 wherein each reinforcement ribbon comprises a para-aramid synthetic fiber.

18. The laser ablation catheter of claim 1 wherein the tubular reinforcement comprises a plurality of reinforcement each having a substantially round transverse cross section and each formed into a tubular braid.

19. The laser ablation catheter of claim 18 wherein each reinforcement wire comprises a metal.

20. The laser ablation catheter of claim 18 wherein each reinforcement wire comprises a para-aramid synthetic fiber.

21. The laser ablation catheter of claim 1 wherein a proximal portion of the outer jacket is adhesively bonded to the catheter tube.

22. A laser ablation catheter, comprising:
a liquid filled waveguide including a catheter tube having an inner layer with a first index of refraction and an optical fluid disposed within and completely filling an inner lumen of the catheter tube, with the optical fluid having a second index of refraction which is greater than the first index of refraction;
a distal optical window disposed in liquid sealed relation to an inner surface of the catheter tube at a distal end of the catheter tube and in optical communication with the optical fluid;
an optical input window disposed in a liquid sealed relation to the inner surface of the catheter tube at a proximal end of the catheter tube and in optical communication with the optical fluid; and
an outer jacket that is disposed over the catheter tube and that has a proximal end that is disposed at a proximal portion of the catheter tube and a distal end that is disposed at an axial position which is substantially adjacent to a distal end of the catheter tube with the outer jacket being secured relative to the catheter tube such that the outer jacket remains substantially fixed along a longitudinal axis thereof relative to the catheter tube, the outer jacket comprising:
an inner lumen with an inner surface, with the inner surface of the inner lumen being configured to slide over an exterior surface of the catheter tube with a close fit therebetween; and
a tubular jacket body formed from a jacket body material that comprises a vapor barrier for the optical fluid and with the tubular jacket body being configured to increase the stiffness and crush resistance of the laser ablation catheter along a length of the outer jacket.

23. The laser ablation catheter of claim 22 wherein the close fit between the outer surface of the catheter tube and the inner surface of the inner lumen of the outer jacket comprises a clearance of about 0.0005 inches to about 0.004 inches.

24. The laser ablation catheter of claim 22 wherein a wall thickness of the outer jacket is thinner than a wall thickness of the catheter tube.

25. The laser ablation catheter of claim 22 wherein the jacket body material comprises polychloro-trifluoro-ethylene.

26. The laser ablation catheter of claim 22 wherein the tubular jacket body tapers from a proximal end of the tubular jacket body to a smaller outer transverse dimension and cross section area at a distal end of the tubular jacket body.

27. The laser ablation catheter of claim 22 further comprising a radiopaque marker which is disposed at a distal portion of the outer jacket, the radiopaque marker allowing for visualization of the distal end of the outer jacket through standard fluoroscopic imaging.

28. The laser ablation catheter of claim 22 wherein the radiopaque marker comprises a tubular band which is secured proximal and substantially adjacent to the distal end of the outer jacket.

29. The laser ablation catheter of claim 22 wherein a proximal portion of the outer jacket is adhesively bonded to the catheter tube.

30. The laser ablation catheter of claim 22 wherein a distal portion of the outer jacket is adhesively bonded to the catheter tube.

31. The laser ablation catheter of claim 22 wherein the outer jacket comprises a substantially constant transverse outer dimension.

32. The laser ablation catheter of claim 22 wherein the tubular jacket body has a longitudinal stiffness greater than a longitudinal stiffness of the catheter tube at a proximal portion thereof.

33. A method of making a liquid core UV laser ablation catheter, comprising:
coating an inner surface of a catheter tube with an optical coating having a first index of refraction;
applying an appropriate thermal cycle to the catheter tube and the optical coating to adhere the optical coating to the inner surface of the catheter tube;
attaching an elongated distal optical window to a distal portion of the catheter tube;
filling the catheter tube with a biocompatible ultraviolet transparent optical fluid having a second index of refraction;
attaching a high energy laser coupler to a proximal portion of the catheter tube with the laser coupler having a laser coupler body, a window connector body being disposed within the optical coupler body, and an optical input window disposed within and secured to the window connector body with the optical window being in optical communication with the optical fluid;
transmitting laser light through the optical fluid to determine the optical performance of the optical coating;

sliding an outer jacket over the catheter tube, the outer jacket having an inner lumen with an inner surface with the inner surface of the inner lumen being configured to slide over an outer surface of the catheter tube with a close fit therebetween; and securing the outer jacket to the catheter tube such that a longitudinal axis of the outer jacket remains substantially fixed in relation the catheter tube, the outer jacket being configured to increase the stiffness and crush resistance of the laser ablation catheter.

34. The method of claim 33 wherein the close fit between the outer surface of the catheter tube and the inner surface of the inner lumen of the outer jacket comprises a clearance of about 0.0005 inches to about 0.004 inches.

35. The method of claim 33 wherein securing the outer jacket to the catheter tube comprises forming a proximal bond section by applying an adhesive between the interior surface of the outer jacket and the outer surface of the catheter tube, the proximal bond section disposed distal and substantially adjacent to the proximal end of the outer jacket.

36. The method of claim 33 wherein sliding the outer jacket over the catheter tube comprises sliding a distal end of the outer jacket to a distance of about 10 cm to about 60 cm proximal of a distal end of the catheter tube.

37. The method of claim 33 wherein sliding the outer jacket over the catheter tube comprises sliding a distal end of the outer jacket up to a distal end of the catheter tube.

\* \* \* \* \*